(12) United States Patent
Roy

(10) Patent No.: US 10,561,788 B2
(45) Date of Patent: Feb. 18, 2020

(54) INFUSION SYSTEMS AND METHODS FOR AUTOMATED EXERCISE MITIGATION

(71) Applicant: MEDTRONIC MINIMED, INC., Northridge, CA (US)

(72) Inventor: Anirban Roy, Agoura Hills, CA (US)

(73) Assignee: Medtronic MiniMed, Inc., Northridge, CA (US)

(*) Notice: Subject to any disclaimer, the term of this patent is extended or adjusted under 35 U.S.C. 154(b) by 283 days.

(21) Appl. No.: 15/717,827

(22) Filed: Sep. 27, 2017

(65) Prior Publication Data

US 2018/0099092 A1   Apr. 12, 2018

Related U.S. Application Data

(60) Provisional application No. 62/405,071, filed on Oct. 6, 2016.

(51) Int. Cl.
*A61M 5/172* (2006.01)
*A61B 5/00* (2006.01)
(Continued)

(52) U.S. Cl.
CPC ....... *A61M 5/1723* (2013.01); *A61B 5/14532* (2013.01); *A61B 5/4839* (2013.01); *A61M 5/142* (2013.01); *A61M 5/14244* (2013.01); *G16H 20/17* (2018.01); *G16H 40/63* (2018.01); *A61B 5/024* (2013.01); *A61B 5/1118* (2013.01); *A61B 5/14546* (2013.01); *A61B 5/7239* (2013.01);
(Continued)

(58) Field of Classification Search
CPC ............ A61M 5/1723; A61M 5/14248; A61M 2005/14208
See application file for complete search history.

(56) References Cited

U.S. PATENT DOCUMENTS 6,248,093 B1   6/2001   Moberg
6,740,072 B2   5/2004   Starkweather et al.
(Continued)

OTHER PUBLICATIONS

Kamuran Turksoy et al: "Classification of Physical Activity : Information to Artificial Pancreas Control Systems in Real Time", Journal of Diabetes Science and Technology, vol. 9, No. 6, Oct. 6, 2015 (Oct. 6, 2015), pp. 1200-1207, XP055436788, US ISSN: 1932-2968, DOI: 10.1177/1932296815609369.
(Continued)

*Primary Examiner* — Laura A Bouchelle
(74) *Attorney, Agent, or Firm* — Lorenz & Kopf, LLP

(57) ABSTRACT

Infusion systems, infusion devices, and related operating methods are provided. An exemplary method of operating an infusion device capable of delivering fluid to a user involves a control system associated with the infusion device obtaining a first measurement indicative of a physiological condition of the user from a first sensing arrangement, obtaining one or more measurements from a second sensing arrangement indicative of a second condition of the user. The control system classifies the second condition as corresponding to one of a plurality of intensity levels based at least in part on the one or more measurements, and thereafter operates the infusion device to deliver the fluid to the user based on the first measurement of the physiological condition in a manner that is influenced by the intensity level classification.

15 Claims, 9 Drawing Sheets

(51) Int. Cl.
    *A61B 5/145*     (2006.01)
    *G16H 20/17*     (2018.01)
    *G16H 40/63*     (2018.01)
    *A61M 5/142*     (2006.01)
    *G16H 20/30*     (2018.01)
    *A61B 5/11*     (2006.01)
    *A61M 5/145*     (2006.01)
    *A61B 5/024*     (2006.01)

(52) U.S. Cl.
CPC ........... *A61B 5/7242* (2013.01); *A61B 5/7264* (2013.01); *A61B 5/7275* (2013.01); *A61B 5/746* (2013.01); *A61M 5/1452* (2013.01); *A61M 2005/14208* (2013.01); *A61M 2202/04* (2013.01); *A61M 2205/3303* (2013.01); *A61M 2205/3327* (2013.01); *A61M 2205/502* (2013.01); *A61M 2205/505* (2013.01); *A61M 2230/04* (2013.01); *A61M 2230/06* (2013.01); *A61M 2230/201* (2013.01); *A61M 2230/63* (2013.01); *G16H 20/30* (2018.01)

(56) References Cited

U.S. PATENT DOCUMENTS

| | | |
|---|---|---|
| 6,827,702 B2 | 12/2004 | Lebel et al. |
| 7,323,142 B2 | 1/2008 | Pendo et al. |
| 7,402,153 B2 | 7/2008 | Steil et al. |
| 8,474,332 B2 | 7/2013 | Bente, IV |
| 2003/0060753 A1 | 3/2003 | Starkweather et al. |
| 2003/0208113 A1* | 11/2003 | Mault ................ A61B 5/14532 600/316 |
| 2009/0164239 A1* | 6/2009 | Hayter ................ G06F 3/04847 705/2 |
| 2014/0066889 A1 | 3/2014 | Grosman et al. |
| 2015/0217052 A1* | 8/2015 | Keenan ................ A61M 5/1723 604/504 |
| 2016/0354543 A1* | 12/2016 | Cinar ................ A61M 5/1723 |

OTHER PUBLICATIONS

Bruce A. Perkins et al: "Type 1 Diabetes and Exercise: Using the Insulin Pump to Maximum Advantage", Canadian Journal of Diabetes, 2006, pp. 72-79, XP055349227, DOI: 10.1016/S1499-2671(06)01008-2 Retrieved from the Internet: URL:http://www.sciencedirect.com/science/article/pii/S1499267106010082/pdfft?md5=9c5cf1834275c039de6b1c40e0f6b592&pid=1-s2.0-S1499267106010082-main.pdf.

Michael C. Riddell et al: "Exercise and the Development of the Artificial Pancreas: One of the More Difficult Series of Hurdles", Journal of Diabetes Science and Technology, vol. 9, No. 6, Oct. 1, 2015 (Oct. 1, 2015), pp. 1217-1226, XP055437054, US ISSN: 1932-2968, DOI: 10.1177/1932296815609370.

\* cited by examiner

INFUSION SYSTEMS AND METHODS FOR AUTOMATED EXERCISE MITIGATION

CROSS-REFERENCE TO RELATED APPLICATION(S)

This application claims the benefit of U.S. Provisional Patent Application Ser. No. 62/405,071, filed Oct. 6, 2016, the entire content of which is incorporated by reference herein.

TECHNICAL FIELD

Embodiments of the subject matter described herein relate generally to medical devices, and more particularly, embodiments of the subject matter relate to automatically adapting control of a fluid infusion device to account for detection of an event or condition that affect a user's sensitivity to the fluid being administered.

BACKGROUND

Infusion pump devices and systems are relatively well known in the medical arts, for use in delivering or dispensing an agent, such as insulin or another prescribed medication, to a patient. A typical infusion pump includes a pump drive system which typically includes a small motor and drive train components that convert rotational motor motion to a translational displacement of a plunger (or stopper) in a reservoir that delivers medication from the reservoir to the body of a user via a fluid path created between the reservoir and the body of a user. Use of infusion pump therapy has been increasing, especially for delivering insulin for diabetics.

Continuous insulin infusion provides greater control of a diabetic's condition, and hence, control schemes are being developed that allow insulin infusion pumps to monitor and regulate a user's blood glucose level in a substantially continuous and autonomous manner, for example, overnight while the user is sleeping. Regulating blood glucose level is complicated by variations in the response time for the type of insulin being used along with each user's individual insulin response. Furthermore, a user's daily activities and experiences may cause that user's insulin response to vary throughout the course of a day or from one day to the next. Thus, it is desirable to account for the anticipated variations or fluctuations in the user's insulin response caused by the user's activities or other condition(s) experienced by the user.

BRIEF SUMMARY

An embodiment of a method of operating an infusion device capable of delivering fluid to regulate a physiological condition of a user is provided. An exemplary method involves a control system of the infusion device obtaining one or more measurements indicative of a second condition of the user different from the physiological condition and classifying the second condition as corresponding to one of a plurality of intensity levels based at least in part on the one or more measurements. The method continues with the control system obtaining a first measurement indicative of the physiological condition of the user from a first sensing arrangement and operating the infusion device to deliver the fluid to the user based on the first measurement of the physiological condition in a manner that is influenced by the one of the plurality of intensity levels.

In another embodiment, a method of operating an insulin infusion device is provided. The method involves obtaining a current glucose measurement for a user from a glucose sensing arrangement, obtaining one or more measurements from an auxiliary sensing arrangement different from the glucose sensing arrangement, detecting an exercise intensity level of a plurality of exercise intensity levels exhibited by the user based at least in part on the one or more measurements, and operating an actuation arrangement of the infusion device to deliver insulin to regulate the glucose level in the body of the user based on the current glucose measurement in a manner that is influenced by the user's exercise intensity level.

In yet another embodiment, an infusion system is provided. The infusion system includes an actuation arrangement operable to deliver insulin to a user, a glucose sensing arrangement to obtain a measured glucose value for the user, a second sensing arrangement to obtain measurement data indicative of exercise by the user, and a control system coupled to the actuation arrangement, the glucose sensing arrangement, and the second sensing arrangement. The control system classifies the exercise by the user as having a first level of a plurality of levels of exercise intensity based on the measurement data, adjusts control information for operating the actuation arrangement based on the first exercise intensity level, and operates the actuation arrangement to deliver the insulin to the user based at least in part on the adjusted control information and the measured glucose value.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures, which may be illustrated for simplicity and clarity and are not necessarily drawn to scale.

DETAILED DESCRIPTION

Figure 1:
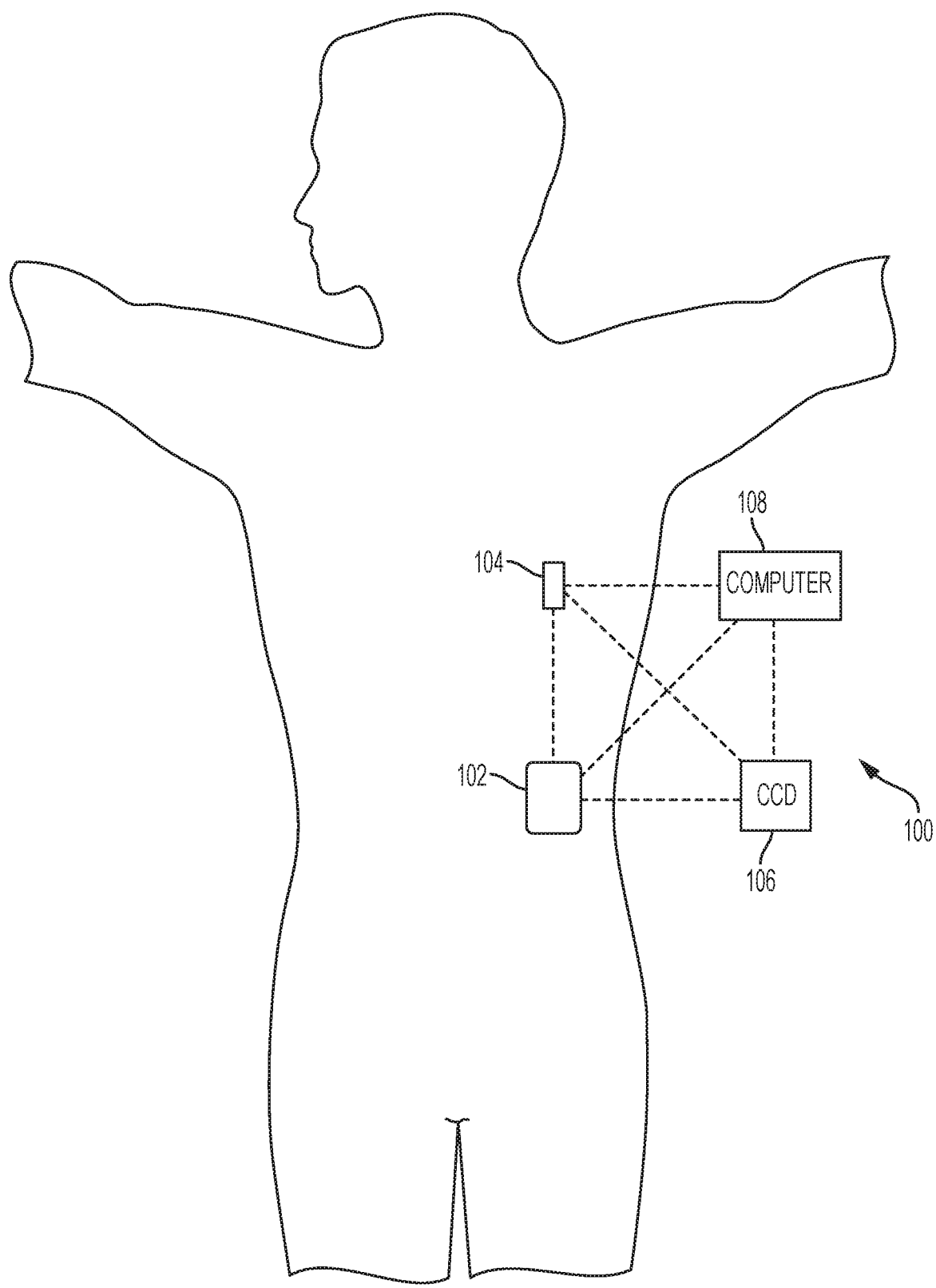
FIG. 1 depicts an exemplary embodiment of an infusion system.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

While the subject matter described herein can be implemented in any electronic device that includes a motor, exemplary embodiments described below are implemented in the form of medical devices, such as portable electronic medical devices. Although many different applications are possible, the following description focuses on a fluid infusion device (or infusion pump) as part of an infusion system deployment. For the sake of brevity, conventional techniques related to infusion system operation, insulin pump and/or infusion set operation, and other functional aspects of the systems (and the individual operating components of the systems) may not be described in detail here. Examples of infusion pumps may be of the type described in, but not limited to, U.S. Pat. Nos. 4,562,751; 4,685,903; 5,080,653; 5,505,709; 5,097,122; 6,485,465; 6,554,798; 6,558,320; 6,558,351; 6,641,533; 6,659,980; 6,752,787; 6,817,990; 6,932,584; and 7,621,893; each of which are herein incorporated by reference.

Embodiments of the subject matter described herein generally relate to fluid infusion devices including a motor that is operable to linearly displace a plunger (or stopper) of a reservoir provided within the fluid infusion device to deliver a dosage of fluid, such as insulin, to the body of a user. In exemplary embodiments, delivery commands (or dosage commands) that govern operation of the motor are determined based on a difference between a measured value for a physiological condition in the body of the user and a target value using closed-loop control to regulate the measured value to the target value. As described in greater detail below in the context of FIGS. 5-10, another condition of the user that is likely to influence the user's response (or sensitivity) to the fluid being administered is detected and classified or otherwise characterized according to how the relative intensity of the detected condition is likely influence the user's response to the fluid. Thereafter, at least some of the control information utilized by the closed-loop control to generate delivery commands and operate the infusion device is automatically adjusted to account for the anticipated change in the user's response to the fluid. As a result, the closed-loop control utilizes the adjusted control information to generate delivery commands and operate the infusion device in accordance with the adjusted control information.

For purposes of explanation, the subject matter may be described herein primarily in the context of detecting and classifying the intensity or level of exercise or other activity a user may be engaged in for purposes of regulating a glucose level in the body of the user by administering dosages of insulin. That said, the subject matter described herein is not necessarily limited to glucose regulation, insulin infusion, or classification of exercise insensitivity levels, and in practice, could be implemented in an equivalent manner with respect to other medications, physiological conditions, and/or the like.

As described in greater detail below, measurements from one or more sensing arrangements, such as, for example, heart rate sensors, accelerometers, lactate sensors, ketone sensors, or the like, are monitored and analyzed to detect exercise by the user and characterize or otherwise classify intensity or level of the exercise based on the measurements. Based on the exercise intensity level, the responsiveness of the closed-loop control may be increased or decreased to compensate for the anticipated change in the user's glucose level resulting from the exercise or the anticipated change in the user's sensitivity to insulin. In this regard, mild to moderate level of exercise generally causes glucose levels to decrease while higher intensity exercise may decrease insulin sensitivity and cause the glucose levels to increase. Accordingly, in response to detecting mild or moderate intensity exercise, control information may be adjusted to make the closed-loop control less aggressive or responsive or otherwise reduce insulin infusion while the user is exercising. However, during anaerobic or higher intensity exercise, the control information is adjusted to be more responsive or proactive to account for potential decreased insulin sensitivity and mitigate exercise-induced hyperglycemia. Thus, the closed-loop control may dynamically adapt as the user's exercise intensity level changes.

In practice, there are numerous different manners in which the closed-loop control information may be adjusted to account for different exercise intensity levels, and the various adjustments may be made independently or in combination. For example, in one or more embodiments, the target glucose level referenced by the closed-loop control scheme may be increased for aerobic exercise or other mild to moderate intensity exercise to decrease the insulin infusion rate, and thereby reduce the likelihood of exercise-induced hypoglycemia. The target glucose level referenced by the closed-loop control scheme may be reduced or otherwise restored to its normal or original value for anaerobic exercise or other high intensity exercise to increase the insulin infusion rate, and thereby reduce the likelihood of exercise-induced hyperglycemia. Additionally or alternatively, one or more insulin delivery limits may be adjusted to allow for the rate or amount of insulin delivery to be increased or decreased to account for the exercise intensity level. For example, a maximum insulin infusion rate or other delivery limits could be increased in response to anaerobic exercise or other high intensity exercise to avoid exercise-induced hyperglycemia but decreased in response to aerobic exercise or lower intensity exercise to avoid exercise-induced hypoglycemia.

In one or more embodiments, one or more parameters of the closed-loop control scheme or algorithm are adjusted to increase or decrease the responsiveness of the closed-loop control to excursions or variations in the user's glucose level. For example, in one or more embodiments, proportional-integral-derivative (PID) closed-loop control is utilized to regulate the user's glucose level, with the time constant associated with the derivative term being adjusted to decrease the responsiveness when the user is engaged in aerobic or other mild to moderate exercise. In this regard, in some embodiments, the time constant adjustment may be dependent upon the trend in the user's glucose level or the value of the derivative of the user's glucose level to adjust responsiveness asymmetrically. For example, the time constant associated with the derivative term may be reduced or scaled downward and utilized when the trend in the user's glucose level is positive during mild to moderate exercise to make the controller less aggressive during exercise and avoid a potential excess amount of on-body active insulin, while maintaining the same time constant when the trend in the user's glucose level is negative to maintain the same level of protection against exercise-induced hypoglycemia. It should be noted that the subject matter is not limited to PID controls, time constant adjustments, or use with the derivative term, and in practice, other PID gain coefficients, time constants, or control parameters could be adjusted, or the subject matter could be implemented in an equivalent manner with control parameters of other non-PID closed-loop control schemes.

Turning now to FIG. 1, one exemplary embodiment of an infusion system 100 includes, without limitation, a fluid infusion device (or infusion pump) 102, a sensing arrangement 104, a command control device (CCD) 106, and a computer 108. The components of an infusion system 100 may be realized using different platforms, designs, and configurations, and the embodiment shown in FIG. 1 is not exhaustive or limiting. In practice, the infusion device 102 and the sensing arrangement 104 are secured at desired locations on the body of a user (or patient), as illustrated in FIG. 1. In this regard, the locations at which the infusion device 102 and the sensing arrangement 104 are secured to the body of the user in FIG. 1 are provided only as a representative, non-limiting, example. The elements of the infusion system 100 may be similar to those described in U.S. Pat. No. 8,674,288, the subject matter of which is hereby incorporated by reference in its entirety.

In the illustrated embodiment of FIG. 1, the infusion device 102 is designed as a portable medical device suitable for infusing a fluid, a liquid, a gel, or other agent into the body of a user. In exemplary embodiments, the infused fluid is insulin, although many other fluids may be administered through infusion such as, but not limited to, HIV drugs, drugs to treat pulmonary hypertension, iron chelation drugs, pain medications, anti-cancer treatments, medications, vitamins, hormones, or the like. In some embodiments, the fluid may include a nutritional supplement, a dye, a tracing medium, a saline medium, a hydration medium, or the like.

The sensing arrangement 104 generally represents the components of the infusion system 100 configured to sense, detect, measure or otherwise quantify a condition of the user, and may include a sensor, a monitor, or the like, for providing data indicative of the condition that is sensed, detected, measured or otherwise monitored by the sensing arrangement. In this regard, the sensing arrangement 104 may include electronics and enzymes reactive to a biological condition, such as a blood glucose level, or the like, of the user, and provide data indicative of the blood glucose level to the infusion device 102, the CCD 106 and/or the computer 108. For example, the infusion device 102, the CCD 106 and/or the computer 108 may include a display for presenting information or data to the user based on the sensor data received from the sensing arrangement 104, such as, for example, a current glucose level of the user, a graph or chart of the user's glucose level versus time, device status indicators, alert messages, or the like. In other embodiments, the infusion device 102, the CCD 106 and/or the computer 108 may include electronics and software that are configured to analyze sensor data and operate the infusion device 102 to deliver fluid to the body of the user based on the sensor data and/or preprogrammed delivery routines. Thus, in exemplary embodiments, one or more of the infusion device 102, the sensing arrangement 104, the CCD 106, and/or the computer 108 includes a transmitter, a receiver, and/or other transceiver electronics that allow for communication with other components of the infusion system 100, so that the sensing arrangement 104 may transmit sensor data or monitor data to one or more of the infusion device 102, the CCD 106 and/or the computer 108.

Still referring to FIG. 1, in various embodiments, the sensing arrangement 104 may be secured to the body of the user or embedded in the body of the user at a location that is remote from the location at which the infusion device 102 is secured to the body of the user. In various other embodiments, the sensing arrangement 104 may be incorporated within the infusion device 102. In other embodiments, the sensing arrangement 104 may be separate and apart from the infusion device 102, and may be, for example, part of the CCD 106. In such embodiments, the sensing arrangement 104 may be configured to receive a biological sample, analyte, or the like, to measure a condition of the user.

In some embodiments, the CCD 106 and/or the computer 108 may include electronics and other components configured to perform processing, delivery routine storage, and to control the infusion device 102 in a manner that is influenced by sensor data measured by and/or received from the sensing arrangement 104. By including control functions in the CCD 106 and/or the computer 108, the infusion device 102 may be made with more simplified electronics. However, in other embodiments, the infusion device 102 may include all control functions, and may operate without the CCD 106 and/or the computer 108. In various embodiments, the CCD 106 may be a portable electronic device. In addition, in various embodiments, the infusion device 102 and/or the sensing arrangement 104 may be configured to transmit data to the CCD 106 and/or the computer 108 for display or processing of the data by the CCD 106 and/or the computer 108.

In some embodiments, the CCD 106 and/or the computer 108 may provide information to the user that facilitates the user's subsequent use of the infusion device 102. For example, the CCD 106 may provide information to the user to allow the user to determine the rate or dose of medication to be administered into the user's body. In other embodiments, the CCD 106 may provide information to the infusion device 102 to autonomously control the rate or dose of medication administered into the body of the user. In some embodiments, the sensing arrangement 104 may be integrated into the CCD 106. Such embodiments may allow the user to monitor a condition by providing, for example, a sample of his or her blood to the sensing arrangement 104 to assess his or her condition. In some embodiments, the sensing arrangement 104 and the CCD 106 may be used for determining glucose levels in the blood and/or body fluids of the user without the use of, or necessity of, a wire or cable connection between the infusion device 102 and the sensing arrangement 104 and/or the CCD 106.

In some embodiments, the sensing arrangement 104 and/or the infusion device 102 are cooperatively configured to utilize a closed-loop system for delivering fluid to the user. Examples of sensing devices and/or infusion pumps utilizing closed-loop systems may be found at, but are not limited to, the following U.S. Pat. Nos. 6,088,608, 6,119,028, 6,589,229, 6,740,072, 6,827,702, 7,323,142, and 7,402,153 or United States Patent Application Publication No. 2014/0066889, all of which are incorporated herein by reference in their entirety. In such embodiments, the sensing arrangement 104 is configured to sense or measure a condition of the user, such as, blood glucose level or the like. The infusion device 102 is configured to deliver fluid in response to the condition sensed by the sensing arrangement 104. In turn, the sensing arrangement 104 continues to sense or otherwise quantify a current condition of the user, thereby allowing the infusion device 102 to deliver fluid continuously in response to the condition currently (or most recently) sensed by the sensing arrangement 104 indefinitely. In some embodiments, the sensing arrangement 104 and/or the infusion device 102 may be configured to utilize the closed-loop system only for a portion of the day, for example only when the user is asleep or awake.

Figure 2:
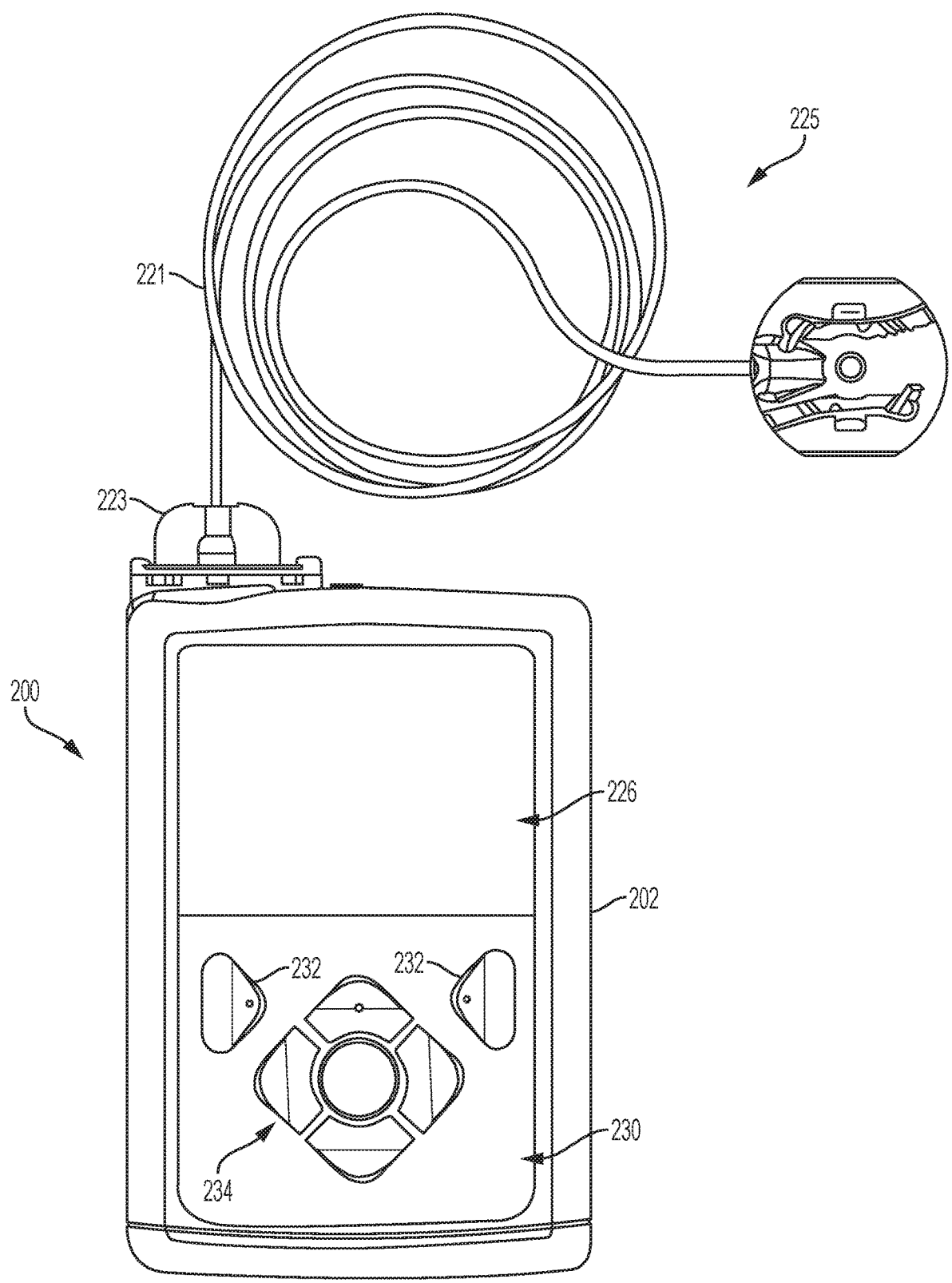
FIG. 2 depicts a plan view of an exemplary embodiment of a fluid infusion device suitable for use in the infusion system of FIG. 1.
Figure 3:
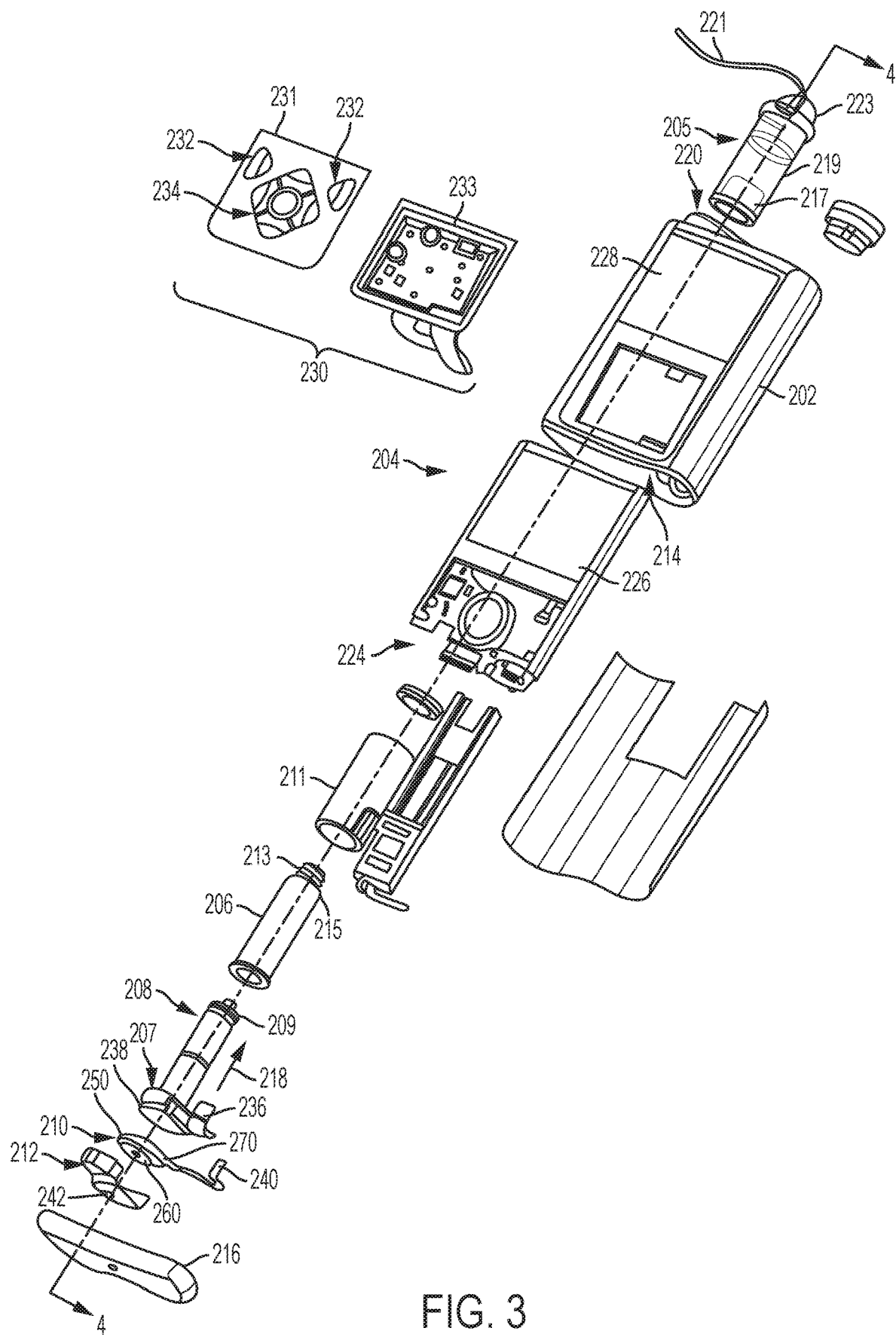
FIG. 3 is an exploded perspective view of the fluid infusion device of FIG. 2.
Figure 4:
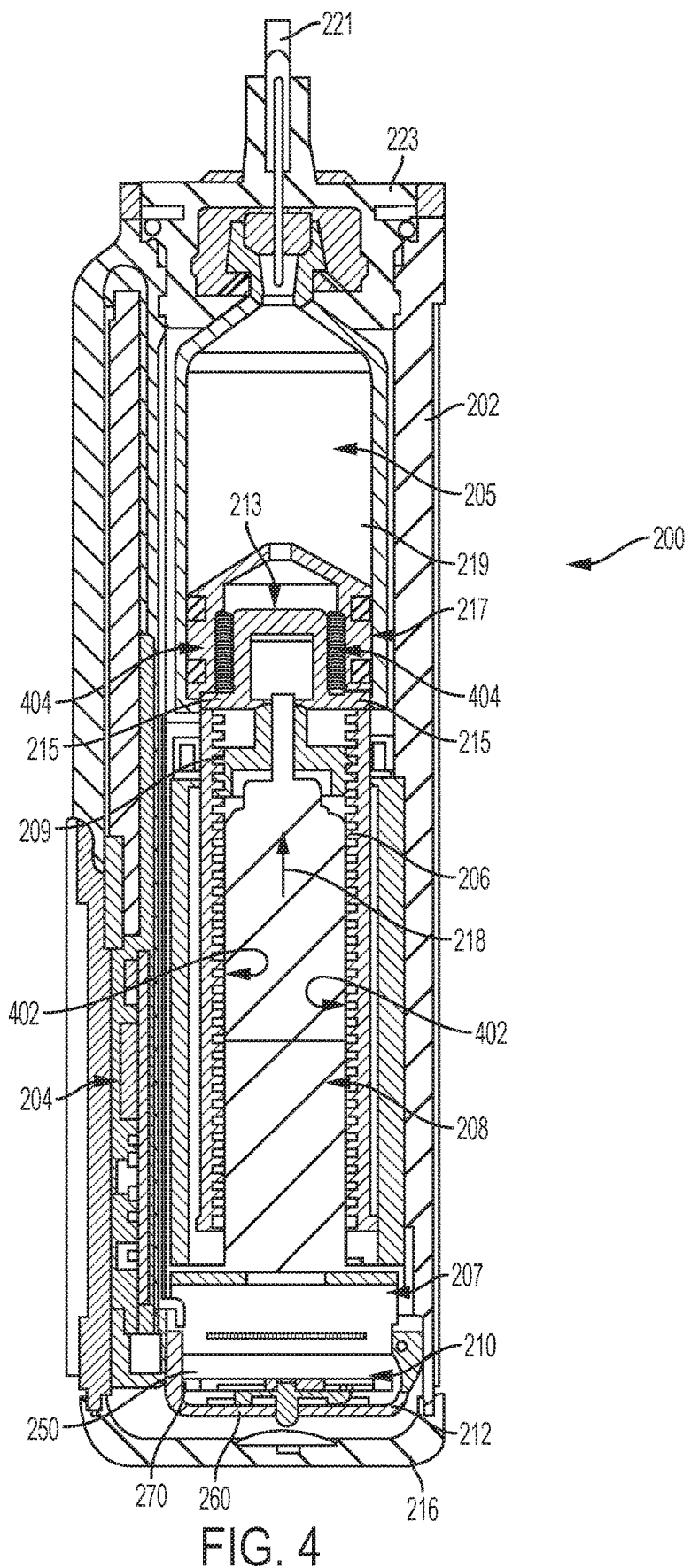
FIG. 4 is a cross-sectional view of the fluid infusion device of FIGS. 2-3 as viewed along line 4-4 in FIG. 3 when assembled with a reservoir inserted in the infusion device.

FIGS. 2-4 depict one exemplary embodiment of a fluid infusion device 200 (or alternatively, infusion pump) suitable for use in an infusion system, such as, for example, as infusion device 102 in the infusion system 100 of FIG. 1. The fluid infusion device 200 is a portable medical device designed to be carried or worn by a patient (or user), and the fluid infusion device 200 may leverage any number of conventional features, components, elements, and characteristics of existing fluid infusion devices, such as, for example, some of the features, components, elements, and/or characteristics described in U.S. Pat. Nos. 6,485,465 and 7,621,893. It should be appreciated that FIGS. 2-4 depict some aspects of the infusion device 200 in a simplified manner; in practice, the infusion device 200 could include additional elements, features, or components that are not shown or described in detail herein.

As best illustrated in FIGS. 2-3, the illustrated embodiment of the fluid infusion device 200 includes a housing 202 adapted to receive a fluid-containing reservoir 205. An opening 220 in the housing 202 accommodates a fitting 223 (or cap) for the reservoir 205, with the fitting 223 being configured to mate or otherwise interface with tubing 221 of an infusion set 225 that provides a fluid path to/from the body of the user. In this manner, fluid communication from the interior of the reservoir 205 to the user is established via the tubing 221. The illustrated fluid infusion device 200 includes a human-machine interface (HMI) 230 (or user interface) that includes elements 232, 234 that can be manipulated by the user to administer a bolus of fluid (e.g., insulin), to change therapy settings, to change user preferences, to select display features, and the like. The infusion device also includes a display element 226, such as a liquid crystal display (LCD) or another suitable display element, that can be used to present various types of information or data to the user, such as, without limitation: the current glucose level of the patient; the time; a graph or chart of the patient's glucose level versus time; device status indicators; etc.

The housing 202 is formed from a substantially rigid material having a hollow interior 214 adapted to allow an electronics assembly 204, a sliding member (or slide) 206, a drive system 208, a sensor assembly 210, and a drive system capping member 212 to be disposed therein in addition to the reservoir 205, with the contents of the housing 202 being enclosed by a housing capping member 216. The opening 220, the slide 206, and the drive system 208 are coaxially aligned in an axial direction (indicated by arrow 218), whereby the drive system 208 facilitates linear displacement of the slide 206 in the axial direction 218 to dispense fluid from the reservoir 205 (after the reservoir 205 has been inserted into opening 220), with the sensor assembly 210 being configured to measure axial forces (e.g., forces aligned with the axial direction 218) exerted on the sensor assembly 210 responsive to operating the drive system 208 to displace the slide 206. In various embodiments, the sensor assembly 210 may be utilized to detect one or more of the following: an occlusion in a fluid path that slows, prevents, or otherwise degrades fluid delivery from the reservoir 205 to a user's body; when the reservoir 205 is empty; when the slide 206 is properly seated with the reservoir 205; when a fluid dose has been delivered; when the infusion pump 200 is subjected to shock or vibration; when the infusion pump 200 requires maintenance.

Depending on the embodiment, the fluid-containing reservoir 205 may be realized as a syringe, a vial, a cartridge, a bag, or the like. In certain embodiments, the infused fluid is insulin, although many other fluids may be administered through infusion such as, but not limited to, HIV drugs, drugs to treat pulmonary hypertension, iron chelation drugs, pain medications, anti-cancer treatments, medications, vitamins, hormones, or the like. As best illustrated in FIGS. 3-4, the reservoir 205 typically includes a reservoir barrel 219 that contains the fluid and is concentrically and/or coaxially aligned with the slide 206 (e.g., in the axial direction 218) when the reservoir 205 is inserted into the infusion pump 200. The end of the reservoir 205 proximate the opening 220 may include or otherwise mate with the fitting 223, which secures the reservoir 205 in the housing 202 and prevents displacement of the reservoir 205 in the axial direction 218 with respect to the housing 202 after the reservoir 205 is inserted into the housing 202. As described above, the fitting 223 extends from (or through) the opening 220 of the housing 202 and mates with tubing 221 to establish fluid communication from the interior of the reservoir 205 (e.g., reservoir barrel 219) to the user via the tubing 221 and infusion set 225. The opposing end of the reservoir 205 proximate the slide 206 includes a plunger 217 (or stopper) positioned to push fluid from inside the barrel 219 of the reservoir 205 along a fluid path through tubing 221 to a user. The slide 206 is configured to mechanically couple or otherwise engage with the plunger 217, thereby becoming seated with the plunger 217 and/or reservoir 205. Fluid is forced from the reservoir 205 via tubing 221 as the drive system 208 is operated to displace the slide 206 in the axial direction 218 toward the opening 220 in the housing 202.

In the illustrated embodiment of FIGS. 3-4, the drive system 208 includes a motor assembly 207 and a drive screw 209. The motor assembly 207 includes a motor that is coupled to drive train components of the drive system 208 that are configured to convert rotational motor motion to a translational displacement of the slide 206 in the axial direction 218, and thereby engaging and displacing the plunger 217 of the reservoir 205 in the axial direction 218. In some embodiments, the motor assembly 207 may also be powered to translate the slide 206 in the opposing direction (e.g., the direction opposite direction 218) to retract and/or detach from the reservoir 205 to allow the reservoir 205 to be replaced. In exemplary embodiments, the motor assembly 207 includes a brushless DC (BLDC) motor having one or more permanent magnets mounted, affixed, or otherwise disposed on its rotor. However, the subject matter described herein is not necessarily limited to use with BLDC motors, and in alternative embodiments, the motor may be realized as a solenoid motor, an AC motor, a stepper motor, a piezoelectric caterpillar drive, a shape memory actuator drive, an electrochemical gas cell, a thermally driven gas cell, a bimetallic actuator, or the like. The drive train components may comprise one or more lead screws, cams, ratchets, jacks, pulleys, pawls, clamps, gears, nuts, slides, bearings, levers, beams, stoppers, plungers, sliders, brackets, guides, bearings, supports, bellows, caps, diaphragms, bags, heaters, or the like. In this regard, although the illustrated embodiment of the infusion pump utilizes a coaxially aligned drive train, the motor could be arranged in an offset or otherwise non-coaxial manner, relative to the longitudinal axis of the reservoir 205.

As best shown in FIG. 4, the drive screw 209 mates with threads 402 internal to the slide 206. When the motor assembly 207 is powered and operated, the drive screw 209 rotates, and the slide 206 is forced to translate in the axial direction 218. In an exemplary embodiment, the infusion pump 200 includes a sleeve 211 to prevent the slide 206 from rotating when the drive screw 209 of the drive system 208 rotates. Thus, rotation of the drive screw 209 causes the slide 206 to extend or retract relative to the drive motor assembly 207. When the fluid infusion device is assembled and operational, the slide 206 contacts the plunger 217 to engage the reservoir 205 and control delivery of fluid from the infusion pump 200. In an exemplary embodiment, the shoulder portion 215 of the slide 206 contacts or otherwise engages the plunger 217 to displace the plunger 217 in the axial direction 218. In alternative embodiments, the slide 206 may include a threaded tip 213 capable of being detachably engaged with internal threads 404 on the plunger 217 of the reservoir 205, as described in detail in U.S. Pat. Nos. 6,248,093 and 6,485,465, which are incorporated by reference herein.

As illustrated in FIG. 3, the electronics assembly 204 includes control electronics 224 coupled to the display element 226, with the housing 202 including a transparent window portion 228 that is aligned with the display element 226 to allow the display 226 to be viewed by the user when the electronics assembly 204 is disposed within the interior 214 of the housing 202. The control electronics 224 generally represent the hardware, firmware, processing logic and/or software (or combinations thereof) configured to control operation of the motor assembly 207 and/or drive system 208, as described in greater detail below in the context of FIG. 5. Whether such functionality is implemented as hardware, firmware, a state machine, or software depends upon the particular application and design constraints imposed on the embodiment. Those familiar with the concepts described here may implement such functionality in a suitable manner for each particular application, but such implementation decisions should not be interpreted as being restrictive or limiting. In an exemplary embodiment, the control electronics 224 includes one or more programmable controllers that may be programmed to control operation of the infusion pump 200.

The motor assembly 207 includes one or more electrical leads 236 adapted to be electrically coupled to the electronics assembly 204 to establish communication between the control electronics 224 and the motor assembly 207. In response to command signals from the control electronics 224 that operate a motor driver (e.g., a power converter) to regulate the amount of power supplied to the motor from a power supply, the motor actuates the drive train components of the drive system 208 to displace the slide 206 in the axial direction 218 to force fluid from the reservoir 205 along a fluid path (including tubing 221 and an infusion set), thereby administering doses of the fluid contained in the reservoir 205 into the user's body. Preferably, the power supply is realized one or more batteries contained within the housing 202. Alternatively, the power supply may be a solar panel, capacitor, AC or DC power supplied through a power cord, or the like. In some embodiments, the control electronics 224 may operate the motor of the motor assembly 207 and/or drive system 208 in a stepwise manner, typically on an intermittent basis; to administer discrete precise doses of the fluid to the user according to programmed delivery profiles.

Referring to FIGS. 2-4, as described above, the user interface 230 includes HMI elements, such as buttons 232 and a directional pad 234, that are formed on a graphic keypad overlay 231 that overlies a keypad assembly 233, which includes features corresponding to the buttons 232, directional pad 234 or other user interface items indicated by the graphic keypad overlay 231. When assembled, the keypad assembly 233 is coupled to the control electronics 224, thereby allowing the HMI elements 232, 234 to be manipulated by the user to interact with the control electronics 224 and control operation of the infusion pump 200, for example, to administer a bolus of insulin, to change therapy settings, to change user preferences, to select display features, to set or disable alarms and reminders, and the like. In this regard, the control electronics 224 maintains and/or provides information to the display 226 regarding program parameters, delivery profiles, pump operation, alarms, warnings, statuses, or the like, which may be adjusted using the HMI elements 232, 234. In various embodiments, the HMI elements 232, 234 may be realized as physical objects (e.g., buttons, knobs, joysticks, and the like) or virtual objects (e.g., using touch-sensing and/or proximity-sensing technologies). For example, in some embodiments, the display 226 may be realized as a touch screen or touch-sensitive display, and in such embodiments, the features and/or functionality of the HMI elements 232, 234 may be integrated into the display 226 and the HMI 230 may not be present. In some embodiments, the electronics assembly 204 may also include alert generating elements coupled to the control electronics 224 and suitably configured to generate one or more types of feedback, such as, without limitation: audible feedback; visual feedback; haptic (physical) feedback; or the like.

Referring to FIGS. 3-4, in accordance with one or more embodiments, the sensor assembly 210 includes a back plate structure 250 and a loading element 260. The loading element 260 is disposed between the capping member 212 and a beam structure 270 that includes one or more beams having sensing elements disposed thereon that are influenced by compressive force applied to the sensor assembly 210 that deflects the one or more beams, as described in greater detail in U.S. Pat. No. 8,474,332, which is incorporated by reference herein. In exemplary embodiments, the back plate structure 250 is affixed, adhered, mounted, or otherwise mechanically coupled to the bottom surface 238 of the drive system 208 such that the back plate structure 250 resides between the bottom surface 238 of the drive system 208 and the housing cap 216. The drive system capping member 212 is contoured to accommodate and conform to the bottom of the sensor assembly 210 and the drive system 208. The drive system capping member 212 may be affixed to the interior of the housing 202 to prevent displacement of the sensor assembly 210 in the direction opposite the direction of force provided by the drive system 208 (e.g., the direction opposite direction 218). Thus, the sensor assembly 210 is positioned between the motor assembly 207 and secured by the capping member 212, which prevents displacement of the sensor assembly 210 in a downward direction opposite the direction of arrow 218, such that the sensor assembly 210 is subjected to a reactionary compressive force when the drive system 208 and/or motor assembly 207 is operated to displace the slide 206 in the axial direction 218 in opposition to the fluid pressure in the reservoir 205. Under normal operating conditions, the compressive force applied to the sensor assembly 210 is correlated with the fluid pressure in the reservoir 205. As shown, electrical leads 240 are adapted to electrically couple the sensing elements of the sensor assembly 210 to the electronics assembly 204 to establish communication to the control electronics 224, wherein the control electronics 224 are configured to measure, receive, or otherwise obtain electrical signals from the sensing elements of the sensor assembly 210 that are indicative of the force applied by the drive system 208 in the axial direction 218.

Figure 5:
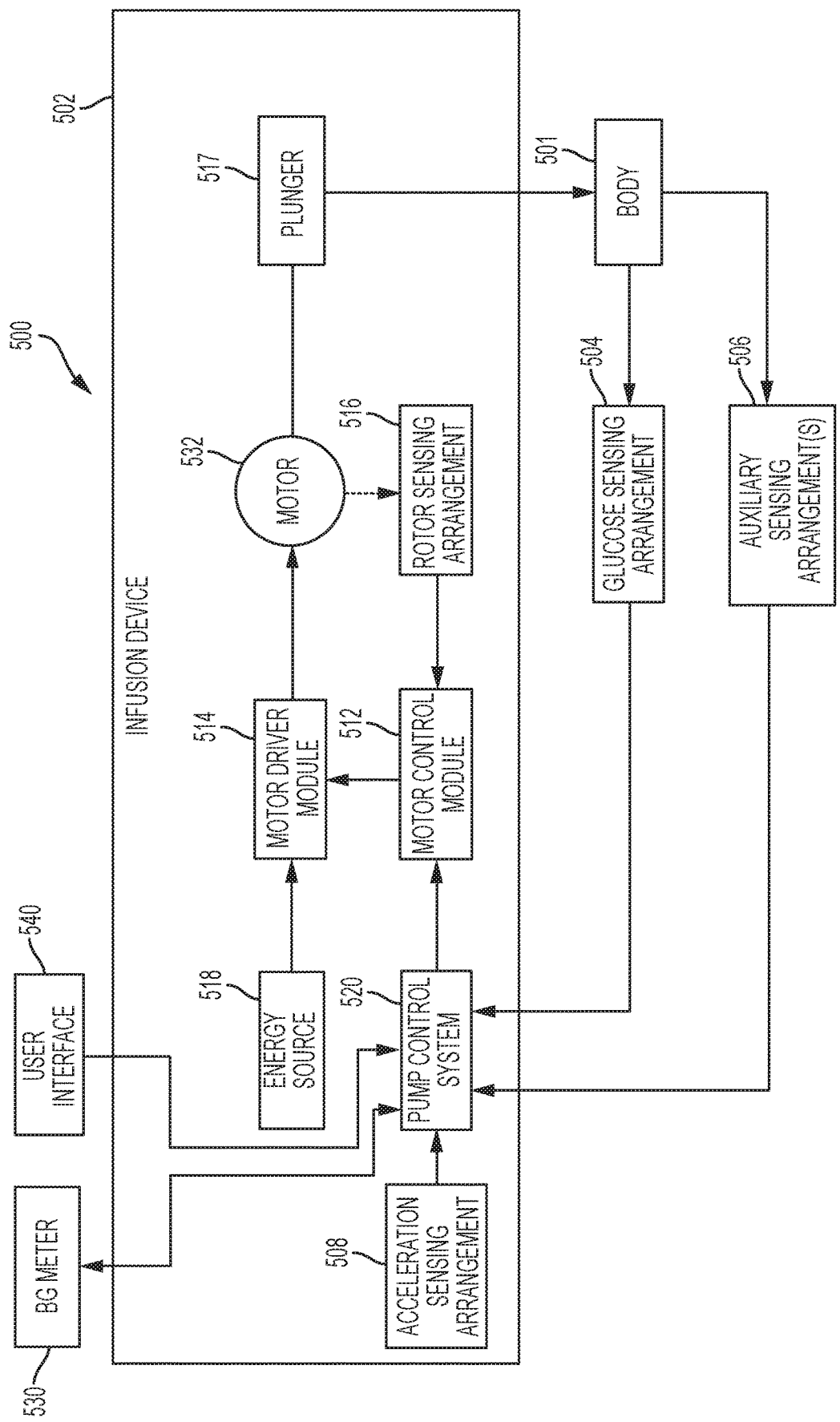
FIG. 5 is a block diagram of an exemplary infusion system suitable for use with a fluid infusion device in one or more embodiments.

FIG. 5 depicts an exemplary embodiment of an infusion system 500 suitable for use with an infusion device 502, such as any one of the infusion devices 102, 200 described above. The infusion system 500 is capable of controlling or otherwise regulating a physiological condition in the body 501 of a user to a desired (or target) value or otherwise maintain the condition within a range of acceptable values in an automated or autonomous manner. In one or more exemplary embodiments, the condition being regulated is sensed, detected, measured or otherwise quantified by a sensing arrangement 504 (e.g., sensing arrangement 504) communicatively coupled to the infusion device 502. However, it should be noted that in alternative embodiments, the condition being regulated by the infusion system 500 may be correlative to the measured values obtained by the sensing arrangement 504. That said, for clarity and purposes of explanation, the subject matter may be described herein in the context of the sensing arrangement 504 being realized as a glucose sensing arrangement that senses, detects, measures or otherwise quantifies the user's glucose level, which is being regulated in the body 501 of the user by the infusion system 500.

In exemplary embodiments, the sensing arrangement 504 includes one or more interstitial glucose sensing elements that generate or otherwise output electrical signals (alternatively referred to herein as measurement signals) having a signal characteristic that is correlative to, influenced by, or otherwise indicative of the relative interstitial fluid glucose level in the body 501 of the user. The output electrical signals are filtered or otherwise processed to obtain a measurement value indicative of the user's interstitial fluid glucose level. In exemplary embodiments, a blood glucose meter 530, such as a finger stick device, is utilized to directly sense, detect, measure or otherwise quantify the blood glucose in the body 501 of the user. In this regard, the blood glucose meter 530 outputs or otherwise provides a measured blood glucose value that may be utilized as a reference measurement for calibrating the sensing arrangement 504 and converting a measurement value indicative of the user's interstitial fluid glucose level into a corresponding calibrated blood glucose value. For purposes of explanation, the calibrated blood glucose value calculated based on the electrical signals output by the sensing element(s) of the sensing arrangement 504 may alternatively be referred to herein as the sensor glucose value, the sensed glucose value, or variants thereof.

In exemplary embodiments, the infusion system 500 also includes one or more additional sensing arrangements 506, 508 configured to sense, detect, measure or otherwise quantify a characteristic of the body 501 of the user that is indicative of a condition in the body 501 of the user. In this regard, in addition to the glucose sensing arrangement 504, one or more auxiliary sensing arrangements 506 may be worn, carried, or otherwise associated with the body 501 of the user to measure characteristics or conditions of the user (or the user's activity) that may influence the user's glucose levels or insulin sensitivity. For example, a heart rate sensing arrangement 506 could be worn on or otherwise associated with the user's body 501 to sense, detect, measure or otherwise quantify the user's heart rate, which, in turn, may be indicative of exercise (and the intensity thereof) that is likely to influence the user's glucose levels or insulin response in the body 501. In yet another embodiment, another invasive, interstitial, or subcutaneous sensing arrangement 506 may be inserted into the body 501 of the user to obtain measurements of another physiological condition that may be indicative of exercise (and the intensity thereof), such as, for example, a lactate sensor, a ketone sensor, or the like. Depending on the embodiment, the auxiliary sensing arrangement(s) 506 could be realized as a standalone component worn by the user, or alternatively, the auxiliary sensing arrangement(s) 506 may be integrated with the infusion device 502 or the glucose sensing arrangement 504.

The illustrated infusion system 500 also includes an acceleration sensing arrangement 508 (or accelerometer) that may be worn on or otherwise associated with the user's body 501 to sense, detect, measure or otherwise quantify an acceleration of the user's body 501, which, in turn, may be indicative of exercise or some other condition in the body 501 that is likely to influence the user's insulin response. While the acceleration sensing arrangement 508 is depicted as being integrated into the infusion device 502 in FIG. 5, in alternative embodiments, the acceleration sensing arrangement 508 may be integrated with another sensing arrangement 504, 506 on the body 501 of the user, or the acceleration sensing arrangement 508 may be realized as a separate standalone component that is worn by the user.

In the illustrated embodiment, the pump control system 520 generally represents the electronics and other components of the infusion device 502 that control operation of the fluid infusion device 502 according to a desired infusion delivery program in a manner that is influenced by the sensed glucose value indicating the current glucose level in the body 501 of the user. For example, to support a closed-loop operating mode, the pump control system 520 maintains, receives, or otherwise obtains a target or commanded glucose value, and automatically generates or otherwise determines dosage commands for operating an actuation arrangement, such as a motor 532, to displace the plunger 517 and deliver insulin to the body 501 of the user based on the difference between the sensed glucose value and the target glucose value. In other operating modes, the pump control system 520 may generate or otherwise determine dosage commands configured to maintain the sensed glucose value below an upper glucose limit, above a lower glucose limit, or otherwise within a desired range of glucose values. In practice, the infusion device 502 may store or otherwise maintain the target value, upper and/or lower glucose limit(s), insulin delivery limit(s), and/or other glucose threshold value(s) in a data storage element accessible to the pump control system 520. As described in greater detail below in the context of FIGS. 6-10, in exemplary embodiments, the pump control system 520 automatically adjusts or adapts one or more parameters or other control information used to generate commands for operating the motor 532 in a manner that is influenced by an exercise intensity level or other user behavior identified based on measurements output by the auxiliary sensing arrangement(s) 506, 508 to regulate the glucose level in the body 501 in a manner that accounts for the likely change in the user's glucose level or insulin response resulting from that level of exercise or activity.

Still referring to FIG. 5, the target glucose value and other threshold glucose values utilized by the pump control system 520 may be received from an external component (e.g., CCD 106 and/or computing device 108) or be input by a user via a user interface element 540 associated with the infusion device 502. In practice, the one or more user interface element(s) 540 associated with the infusion device 502 typically include at least one input user interface element, such as, for example, a button, a keypad, a keyboard, a knob, a joystick, a mouse, a touch panel, a touchscreen, a microphone or another audio input device, and/or the like. Additionally, the one or more user interface element(s) 540 include at least one output user interface element, such as, for example, a display element (e.g., a light-emitting diode or the like), a display device (e.g., a liquid crystal display or the like), a speaker or another audio output device, a haptic feedback device, or the like, for providing notifications or other information to the user. It should be noted that although FIG. 5 depicts the user interface element(s) 540 as being separate from the infusion device 502, in practice, one or more of the user interface element(s) 540 may be integrated with the infusion device 502. Furthermore, in some embodiments, one or more user interface element(s) 540 are integrated with the sensing arrangement 504 in addition to and/or in alternative to the user interface element(s) 540 integrated with the infusion device 502. The user interface element(s) 540 may be manipulated by the user to operate the infusion device 502 to deliver correction boluses, adjust target and/or threshold values, modify the delivery control scheme or operating mode, and the like, as desired.

Still referring to FIG. 5, in the illustrated embodiment, the infusion device 502 includes a motor control module 512 coupled to a motor 532 (e.g., motor assembly 207) that is operable to displace a plunger 517 (e.g., plunger 217) in a reservoir (e.g., reservoir 205) and provide a desired amount of fluid to the body 501 of a user. In this regard, displacement of the plunger 517 results in the delivery of a fluid, such as insulin, that is capable of influencing the user's physiological condition to the body 501 of the user via a fluid delivery path (e.g., via tubing 221 of an infusion set 225). A motor driver module 514 is coupled between an energy source 518 and the motor 532. The motor control module 512 is coupled to the motor driver module 514, and the motor control module 512 generates or otherwise provides command signals that operate the motor driver module 514 to provide current (or power) from the energy source 518 to the motor 532 to displace the plunger 517 in response to receiving, from a pump control system 520, a dosage command indicative of the desired amount of fluid to be delivered.

In exemplary embodiments, the energy source 518 is realized as a battery housed within the infusion device 502 (e.g., within housing 202) that provides direct current (DC) power. In this regard, the motor driver module 514 generally represents the combination of circuitry, hardware and/or other electrical components configured to convert or otherwise transfer DC power provided by the energy source 518 into alternating electrical signals applied to respective phases of the stator windings of the motor 532 that result in current flowing through the stator windings that generates a stator magnetic field and causes the rotor of the motor 532 to rotate. The motor control module 512 is configured to receive or otherwise obtain a commanded dosage from the pump control system 520, convert the commanded dosage to a commanded translational displacement of the plunger 517, and command, signal, or otherwise operate the motor driver module 514 to cause the rotor of the motor 532 to rotate by an amount that produces the commanded translational displacement of the plunger 517. For example, the motor control module 512 may determine an amount of rotation of the rotor required to produce translational displacement of the plunger 517 that achieves the commanded dosage received from the pump control system 520. Based on the current rotational position (or orientation) of the rotor with respect to the stator that is indicated by the output of the rotor sensing arrangement 516, the motor control module 512 determines the appropriate sequence of alternating electrical signals to be applied to the respective phases of the stator windings that should rotate the rotor by the determined amount of rotation from its current position (or orientation). In embodiments where the motor 532 is realized as a BLDC motor, the alternating electrical signals commutate the respective phases of the stator windings at the appropriate orientation of the rotor magnetic poles with respect to the stator and in the appropriate order to provide a rotating stator magnetic field that rotates the rotor in the desired direction. Thereafter, the motor control module 512 operates the motor driver module 514 to apply the determined alternating electrical signals (e.g., the command signals) to the stator windings of the motor 532 to achieve the desired delivery of fluid to the user.

When the motor control module 512 is operating the motor driver module 514, current flows from the energy source 518 through the stator windings of the motor 532 to produce a stator magnetic field that interacts with the rotor magnetic field. In some embodiments, after the motor control module 512 operates the motor driver module 514 and/or motor 532 to achieve the commanded dosage, the motor control module 512 ceases operating the motor driver module 514 and/or motor 532 until a subsequent dosage command is received. In this regard, the motor driver module 514 and the motor 532 enter an idle state during which the motor driver module 514 effectively disconnects or isolates the stator windings of the motor 532 from the energy source 518. In other words, current does not flow from the energy source 518 through the stator windings of the motor 532 when the motor 532 is idle, and thus, the motor 532 does not consume power from the energy source 518 in the idle state, thereby improving efficiency.

Depending on the embodiment, the motor control module 512 may be implemented or realized with a general purpose processor, a microprocessor, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. In exemplary embodiments, the motor control module 512 includes or otherwise accesses a data storage element or memory, including any sort of random access memory (RAM), read only memory (ROM), flash memory, registers, hard disks, removable disks, magnetic or optical mass storage, or any other short or long term storage media or other non-transitory computer-readable medium, which is capable of storing programming instructions for execution by the motor control module 512. The computer-executable programming instructions, when read and executed by the motor control module 512, cause the motor control module 512 to perform or otherwise support the tasks, operations, functions, and processes described herein.

It should be appreciated that FIG. 5 is a simplified representation of the infusion device 502 for purposes of explanation and is not intended to limit the subject matter described herein in any way. In this regard, depending on the embodiment, some features and/or functionality of the sensing arrangement 504 may implemented by or otherwise integrated into the pump control system 520, or vice versa. Similarly, in practice, the features and/or functionality of the motor control module 512 may implemented by or otherwise integrated into the pump control system 520, or vice versa. Furthermore, the features and/or functionality of the pump control system 520 may be implemented by control electronics 224 located in the fluid infusion device 502, while in alternative embodiments, the pump control system 520 may be implemented by a remote computing device that is physically distinct and/or separate from the infusion device 502, such as, for example, the CCD 106 or the computing device 108.

Figure 6:
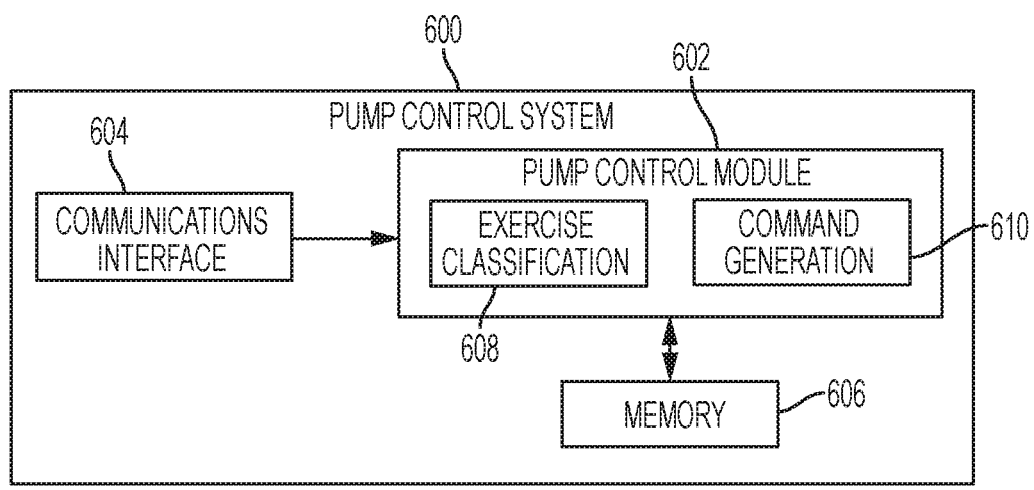
FIG. 6 is a block diagram of an exemplary pump control system suitable for use in the infusion device in the infusion system of FIG. 5 in one or more embodiments.

FIG. 6 depicts an exemplary embodiment of a pump control system 600 suitable for use as the pump control system 520 in FIG. 5 in accordance with one or more embodiments. The illustrated pump control system 600 includes, without limitation, a pump control module 602, a communications interface 604, and a data storage element (or memory) 606. The pump control module 602 is coupled to the communications interface 604 and the memory 606, and the pump control module 602 is suitably configured to support the operations, tasks, and/or processes described herein. In various embodiments, the pump control module 602 is also coupled to one or more user interface elements (e.g., user interface 230, 540) for receiving user inputs (e.g., target glucose values or other glucose thresholds) and providing notifications, alerts, or other therapy information to the user.

The communications interface 604 generally represents the hardware, circuitry, logic, firmware and/or other components of the pump control system 600 that are coupled to the pump control module 602 and configured to support communications between the pump control system 600 and the various sensing arrangements 504, 506, 508. In this regard, the communications interface 604 may include or otherwise be coupled to one or more transceiver modules capable of supporting wireless communications between the pump control system 520, 600 and the sensing arrangement 504, 506, 508. For example, the communications interface 604 may be utilized to receive sensor measurement values or other measurement data from each sensing arrangement 504, 506, 508 in an infusion system 500. In other embodiments, the communications interface 604 may be configured to support wired communications to/from the sensing arrangement(s) 504, 506, 508. In various embodiments, the communications interface 604 may also support communications with another electronic device (e.g., CCD 106 and/or computer 108) in an infusion system (e.g., to upload sensor measurement values to a server or other computing device, receive control information from a server or other computing device, and the like).

The pump control module 602 generally represents the hardware, circuitry, logic, firmware and/or other component of the pump control system 600 that is coupled to the communications interface 604 and configured to determine dosage commands for operating the motor 532 to deliver fluid to the body 501 based on measurement data received from the sensing arrangements 504, 506, 508 and perform various additional tasks, operations, functions and/or operations described herein. For example, in exemplary embodiments, pump control module 602 implements or otherwise executes a command generation application 610 that supports one or more autonomous operating modes and calculates or otherwise determines dosage commands for operating the motor 532 of the infusion device 502 in an autonomous operating mode based at least in part on a current measurement value for a condition in the body 501 of the user. For example, in a closed-loop operating mode, the command generation application 610 may determine a dosage command for operating the motor 532 to deliver insulin to the body 501 of the user based at least in part on the current glucose measurement value most recently received from the sensing arrangement 504 to regulate the user's blood glucose level to a target reference glucose value. Additionally, the command generation application 610 may generate dosage commands for boluses that are manually-initiated or otherwise instructed by a user via a user interface element.

In exemplary embodiments, the pump control module 602 also implements or otherwise executes an exercise classification application 608 that analyzes measurement data received from one or more auxiliary sensing arrangement(s) (e.g., sensing arrangements 506, 508) to detect whether or not the user is engaged in exercise, and characterize or otherwise classify the intensity or type of exercise the user is engaged in. For example, in some embodiments, the exercise classification application 608 may identify whether the user is sedentary, or if not, classify the type of exercise the user is engaged in as aerobic or anaerobic. In yet other embodiments, the exercise classification application 608 may classify the relative intensity of exercise the user is engaged in, such as, for example, a mild level of exercise intensity, a moderate level of exercise intensity, a high level of exercise intensity, and the like. In one or more embodiments, based on the level of exercise detected, the exercise classification application 608 adjusts or otherwise modifies values for one or more parameters utilized by the command generation application 610 when determining dosage commands, for example, by modifying a parameter value at a register or location in memory 606 referenced by the command generation application 610. In yet other embodiments, the exercise classification application 608 may output or otherwise provide an indication of the relative exercise level to the command generation application 610, which, in turn, automatically adjusts the manner in which dosage commands are generated to regulate glucose in a manner that accounts for the indicated exercise level.

Still referring to FIG. 6, depending on the embodiment, the pump control module 602 may be implemented or realized with a general purpose processor, a microprocessor, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. In this regard, the steps of a method or algorithm described in connection with the embodiments disclosed herein may be embodied directly in hardware, in firmware, in a software module executed by the pump control module 602, or in any practical combination thereof. In exemplary embodiments, the pump control module 602 includes or otherwise accesses the data storage element or memory 606, which may be realized using any sort of non-transitory computer-readable medium capable of storing programming instructions for execution by the pump control module 602. The computer-executable programming instructions, when read and executed by the pump control module 602, cause the pump control module 602 to implement or otherwise generate the applications 608, 610 and perform tasks, operations, functions, and processes described herein.

It should be understood that FIG. 6 is a simplified representation of a pump control system 600 for purposes of explanation and is not intended to limit the subject matter described herein in any way. For example, in some embodiments, the features and/or functionality of the motor control module 512 may be implemented by or otherwise integrated into the pump control system 600 and/or the pump control module 602, for example, by the command generation application 610 converting the dosage command into a corresponding motor command, in which case, the separate motor control module 512 may be absent from an embodiment of the infusion device 502.

Figure 7:
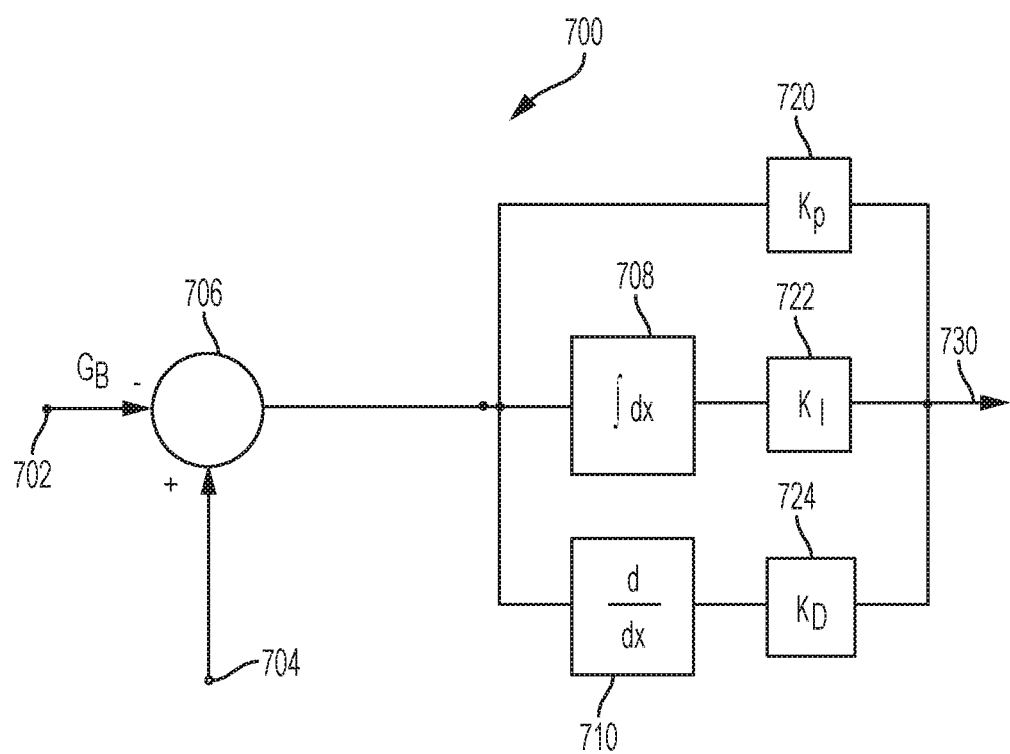
FIG. 7 is a block diagram of a closed-loop control system that may be implemented or otherwise supported by the pump control system in the fluid infusion device of FIGS. 5-6 in one or more exemplary embodiments.

FIG. 7 depicts an exemplary closed-loop control system 700 that may be implemented by a pump control system 520, 600 to provide a closed-loop operating mode that autonomously regulates a condition in the body of a user to a reference (or target) value. It should be appreciated that FIG. 7 is a simplified representation of the control system 700 for purposes of explanation and is not intended to limit the subject matter described herein in any way.

In exemplary embodiments, the control system 700 receives or otherwise obtains a target glucose value at input 702. In some embodiments, the target glucose value may be stored or otherwise maintained by the infusion device 502 (e.g., in memory 606), however, in some alternative embodiments, the target value may be received from an external component (e.g., CCD 106 and/or computer 108). In one or more embodiments, the target glucose value may be calculated or otherwise determined prior to entering the closed-loop operating mode based on one or more patient-specific control parameters. For example, the target blood glucose value may be calculated based at least in part on a patient-specific reference basal rate and a patient-specific daily insulin requirement, which are determined based on historical delivery information over a preceding interval of time (e.g., the amount of insulin delivered over the preceding 24 hours). The control system 700 also receives or otherwise obtains a current glucose measurement value (e.g., the most recently obtained sensor glucose value) from the sensing arrangement 504 at input 704. The illustrated control system 700 implements or otherwise provides proportional-integral-derivative (PID) control to determine or otherwise generate delivery commands for operating the motor 510 based at least in part on the difference between the target glucose value and the current glucose measurement value. In this regard, the PID control attempts to minimize the difference between the measured value and the target value, and thereby regulates the measured value to the desired value. PID control parameters are applied to the difference between the target glucose level at input 702 and the measured glucose level at input 704 to generate or otherwise determine a dosage (or delivery) command provided at output 730. Based on that delivery command, the motor control module 512 operates the motor 510 to deliver insulin to the body of the user to influence the user's glucose level, and thereby reduce the difference between a subsequently measured glucose level and the target glucose level.

The illustrated control system 700 includes or otherwise implements a summation block 706 configured to determine a difference between the target value obtained at input 702 and the measured value obtained from the sensing arrangement 504 at input 704, for example, by subtracting the target value from the measured value. The output of the summation block 706 represents the difference between the measured and target values, which is then provided to each of a proportional term path, an integral term path, and a derivative term path. The proportional term path includes a gain block 720 that multiplies the difference by a proportional gain coefficient, $K_P$, to obtain the proportional term. The integral term path includes an integration block 708 that integrates the difference and a gain block 722 that multiplies the integrated difference by an integral gain coefficient, $K_I$, to obtain the integral term. The derivative term path includes a derivative block 710 that determines the derivative of the difference and a gain block 724 that multiplies the derivative of the difference by a derivative gain coefficient, $K_D$, to obtain the derivative term. The proportional term, the integral term, and the derivative term are then added or otherwise combined to obtain a delivery command that is utilized to operate the motor at output 730. Various implementation details pertaining to closed-loop PID control and determining gain coefficients are described in greater detail in U.S. Pat. No. 7,402,153, which is incorporated by reference.

In one or more exemplary embodiments, the PID gain coefficients are user-specific (or patient-specific) and dynamically calculated or otherwise determined prior to entering the closed-loop operating mode based on historical insulin delivery information (e.g., amounts and/or timings of previous dosages, historical correction bolus information, or the like), historical sensor measurement values, historical reference blood glucose measurement values, user-reported or user-input events (e.g., meals, exercise, and the like), and the like. In this regard, one or more patient-specific control parameters (e.g., an insulin sensitivity factor, a daily insulin requirement, an insulin limit, a reference basal rate, a reference fasting glucose, an active insulin action duration, pharmodynamical time constants, or the like) may be utilized to compensate, correct, or otherwise adjust the PID gain coefficients to account for various operating conditions experienced and/or exhibited by the infusion device 502. The PID gain coefficients may be maintained by the memory 606 accessible to the pump control module 602. In this regard, the memory 606 may include a plurality of registers associated with the control parameters for the PID control. For example, a first parameter register may store the target glucose value and be accessed by or otherwise coupled to the summation block 706 at input 702, and similarly, a second parameter register accessed by the proportional gain block 720 may store the proportional gain coefficient, a third parameter register accessed by the integration gain block 722 may store the integration gain coefficient, and a fourth parameter register accessed by the derivative gain block 724 may store the derivative gain coefficient.

As described in greater detail below, in one or more exemplary embodiments, one or more parameters of the closed-loop control system 700 are automatically adjusted or adapted to account for the intensity or type of exercise the user is engaged in to account for potential changes in the user's glucose level or insulin sensitivity resulting from the exercise. For example, in one or more embodiments, the target glucose value 702 may be increased for aerobic exercise or other mild to moderate intensity exercise to achieve a reduction in the insulin infusion rate, and thereby reduce the likelihood of exercise-induced hypoglycemia. Conversely, after the target glucose value 702 has been increased, once the exercise level transitions to anaerobic exercise or other high intensity exercise, the target glucose value 702 may be reverted to the original or default preprogrammed value to allow the insulin infusion rate to be increased, and thereby reduce the likelihood of exercise-induced hyperglycemia. Additionally or alternatively, the time constant or gain coefficient associated with one or more paths of the closed-loop control system 700 may be adjusted to tune the responsiveness to deviations between the measured glucose value 704 and the target glucose value 702. For example, the time constant associated with the derivative block 710 or derivative term path may be reduced during aerobic or other mild to moderate exercise to make the closed-loop control less aggressive during such exercise and avoid an excess infusion of insulin in response to an increase in the user's glucose level that could potentially be mitigated by the exercise.

Figure 8:
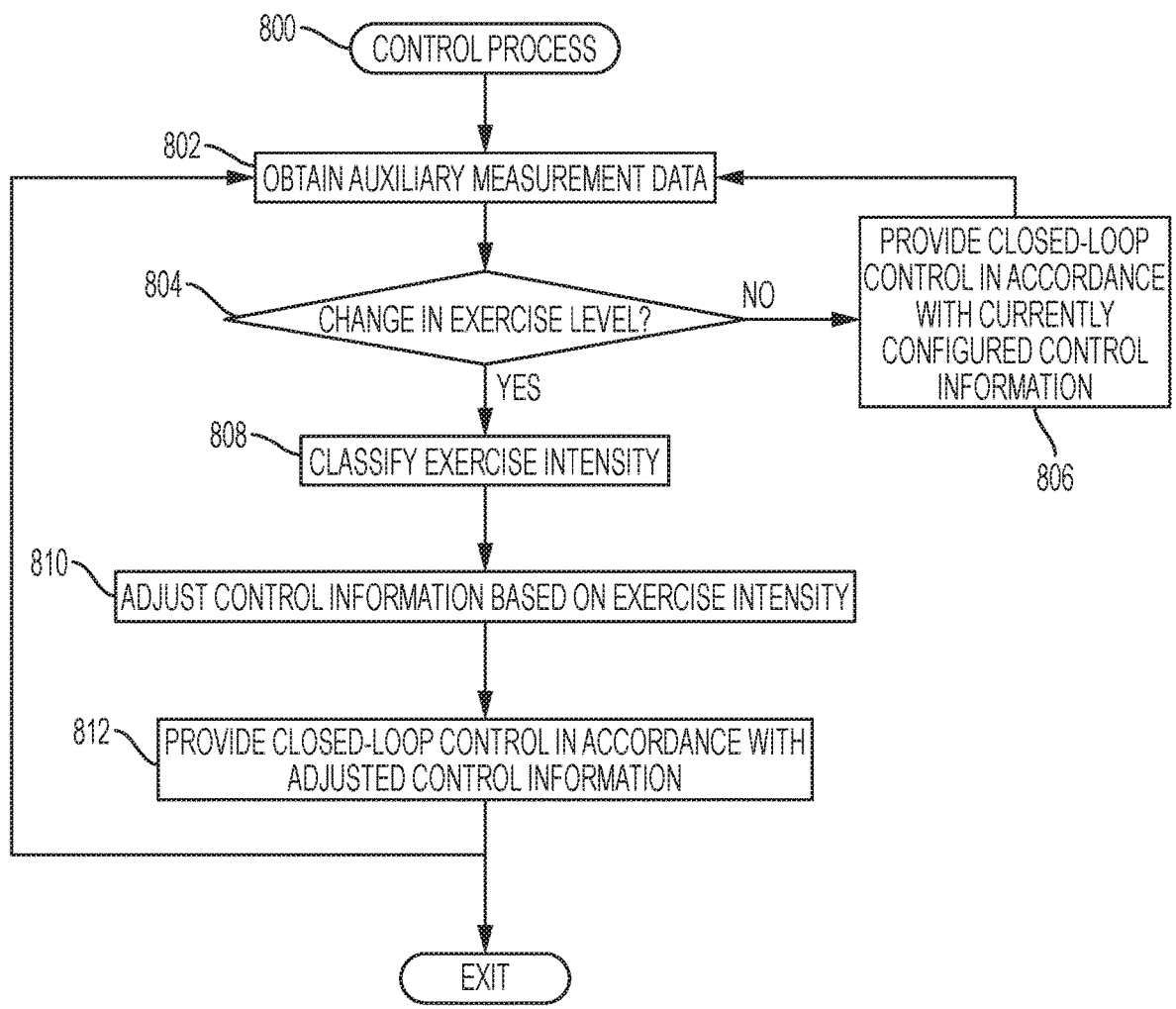
FIG. 8 is a flow diagram of an exemplary control process suitable for use with a fluid infusion device to dynamically adjust controls based on a user's exercise intensity level.

FIG. 8 depicts an exemplary control process 800 suitable for implementation to dynamically adjust closed-loop control information based on measurement data from auxiliary sensors to automatically account for a condition in the body of the user that is likely to influence a user's glucose level or insulin response. The various tasks performed in connection with the control process 800 may be performed by hardware, firmware, software executed by processing circuitry, or any combination thereof. For illustrative purposes, the following description refers to elements mentioned above in connection with FIGS. 1-7. In practice, portions of the control process 800 may be performed by different elements of an infusion system, such as, for example, an infusion device 502, one or more sensing arrangements 504, 506, 508, and/or a pump control system 520, 600. It should be appreciated that the control process 800 may include any number of additional or alternative tasks, the tasks need not be performed in the illustrated order and/or the tasks may be performed concurrently, and/or the control process 800 may be incorporated into a more comprehensive procedure or process having additional functionality not described in detail herein. Moreover, one or more of the tasks shown and described in the context of FIG. 8 could be omitted from a practical embodiment of the control process 800 as long as the intended overall functionality remains intact.

The control process 800 receives or otherwise obtains auxiliary measurement data and monitors or otherwise analyzes the auxiliary measurement data to detect a change in the user's activity level or exercise (tasks 802, 804). In this regard, the pump control system 520, 600 and/or exercise classification application 608 obtain measurement values from the non-glucose sensing arrangement(s) 506, 508 and analyze the measurement values for patterns, trends, or other characteristics indicative of a change in the user's level of activity or exercise. For example, the pump control system 520, 600 and/or exercise classification application 608 may analyze acceleration measurement values from the acceleration sensing arrangement 508 in connection with other measurement values from one or more other auxiliary sensing arrangements 506, such as, for example, heart rate measurements, lactate measurements, ketone measurements, or the like to detect exercise or a change in activity level from a sedentary state based on acceleration measurement values indicating increased motion or activity by the user concurrently to changes in the other measurement values indicative of exercise. In some embodiments, the pump control system 520, 600 and/or exercise classification application 608 may utilize neural networks, machine learning, or other artificial intelligence to detect exercise based on concurrent combinations or trends in different measurement values from different sensing arrangements 506, 508.

In yet other embodiments, the pump control system 520, 600 and/or exercise classification application 608 may utilize a mathematical formula to calculate a metric indicative of an exercise intensity level as a function of the different sensor measurement values from the different sensing arrangements 506, 508. In this regard, a mathematical model may be developed by collecting measurement data from the different sensing arrangements 506, 508 for different users participating in different levels of exercise and analyzing the experimental measurement data to arrive at a mathematical function that maps sensor measurement values to a corresponding exercise intensity metric value. For example, a system of differential equations may be utilized to capture the effects of insulin and exercise on glucose levels as a function of measured lactate levels, measured ketone levels, measured acceleration or motion, and potential other biomarkers or characteristics measurable using auxiliary sensing arrangements.

For example, in one embodiment, the pump control system 520, 600 and/or exercise classification application 608 may model the exercise intensity as a function of an input acceleration measurement value, an input lactate measurement value, and an input ketone measurement value. In exemplary embodiments, the input values are first normalized to a range of values between 0 and 100 using the equation $$m_{norm} = \frac{m - m_{minimum}}{m_{maximum} - m_{minimum}},$$

where $m_{norm}$ is the normalized measurement value, m is the input measurement value, $m_{maximum}$ is the maximum value that the measurement value can reach, and $m_{minimum}$ is the minimum value that the measurement value can reach. In order to capture the dynamics of each input signal, a first order differential equation can be utilized to derive a parameter that captures the dynamics of the input signal. For example, the equation $$\frac{d(m)}{dt} = \frac{1}{\tau_M}(m_{norm} - m)$$

can be utilized to derive a smoothed signal for the input variable, where $\tau_M$ is the parameter which captures the dynamics of the variable and can be trained based on data using machine learning techniques. The smoothed input signals for the various input variables can be combined to provide a first order differential equation function for the exercise intensity value $$\frac{d(E)}{dt} = \frac{1}{\tau_E}(k_A \cdot A + k_L \cdot L + k_K \cdot K - E),$$

where A is the smoothed acceleration measurement signal, L is the smoothed lactate measurement signal, K is the smoothed ketone measurement signal, and E represents the exercise intensity, where $k_M$, $k_L$, and $k_K$ are adjustable gain parameters and $\tau_E$ is a time constant which are determined or otherwise trained based on data using machine learning techniques to arrive at an equation for the exercise intensity value as a function of an input acceleration measurement value, an input lactate measurement value and an input ketone measurement value.

Still referring to FIG. 8, in the absence of a change in exercise intensity level, the control process 800 continues by providing closed-loop control of the user's glucose level in accordance with the current control information (task 806). In this regard, while a user is in a sedentary state or otherwise not engaging in any significant amount of exercise or activity, the pump control system 520, 600 and/or the command generation application 610 generates dosage commands (or motor commands) for operating the infusion device 502 in accordance with the normal, default, or preprogrammed control information for the closed-loop operating mode. In other words, the closed-loop control system 700 utilizes the target glucose value 702, gain coefficients, time constants, and other parameters that were programmed by a user and/or calculated for the user without any adjustments for exercise level. The loop defined by tasks 802, 804, and 806 may repeat indefinitely to provide closed-loop control and regulate the measured glucose value to the target glucose value for the user as described above.

In response to detecting a change in the user's exercise or activity level, the control process 800 characterizes or otherwise classifies the user's current exercise intensity and automatically adjusts or otherwise modifies control information for the infusion device to account for the user's current exercise intensity level (tasks 808, 810). In this regard, the pump control system 520, 600 and/or exercise classification application 608 analyzes the auxiliary measurement data from the auxiliary sensing arrangements 506, 508 to determine what type of exercise the user is engaged in or otherwise determines a relative intensity of the exercise. For example, in some embodiments, the pump control system 520, 600 and/or exercise classification application 608 characterizes the user's exercise intensity as one of aerobic exercise, anaerobic exercise, or no exercise (or sedentary). In yet other embodiments, the pump control system 520, 600 and/or exercise classification application 608 characterizes the user's exercise intensity as one of a plurality of different levels of exercise intensity, such as, for example, mild intensity, moderate intensity, high intensity, and the like.

In exemplary embodiments, one or more control parameters utilized by the command generation application 610 and/or the closed-loop control system 700 are automatically adjusted based on the resulting class or category of exercise intensity that the user's current activity is classified within. In this regard, different levels or categories of exercise intensity levels may be associated with different control parameters that are to be adjusted, different scaling factors or values by which to adjust those control parameters, and the like. For example, in one or more embodiments, only one control parameter may be adjusted when the current exercise is classified as mild intensity, with one or more additional parameters being adjusted to further adapt the closed-loop controls when the current exercise is classified as moderate intensity. In yet other embodiments, the magnitude or amount by which a control parameter is adjusted may vary depending on the class or category of exercise intensity level.

Still referring to FIG. 8, after adjusting the control information to account for the current exercise intensity, the control process 800 provides closed-loop control of the user's glucose level in accordance with the adjusted control information (task 812). In this regard, the rate or amount of insulin infusion delivered based on the current glucose measurement value 704 may be increased or decreased to account for the anticipated change in the user's glucose level or insulin response due to exercise. While the user is engaging in the same class or type of exercise, the loop defined by tasks 802, 804 and 806 repeats to maintain closed-loop control in accordance with the adjusted control information for the duration of the exercise, until a change in the user's exercise level is detected. Thereafter, the control process 800 proceeds by adjusting the control information to account for an increased exercise intensity, or alternatively, to revert back to the original or default control parameters when the user resumes a sedentary state (tasks 808, 810). Thus, the control process 800 may repeat indefinitely to dynamically adapt the closed-loop control parameters to account for fluctuations in the user's activity levels over time.

Figure 9:
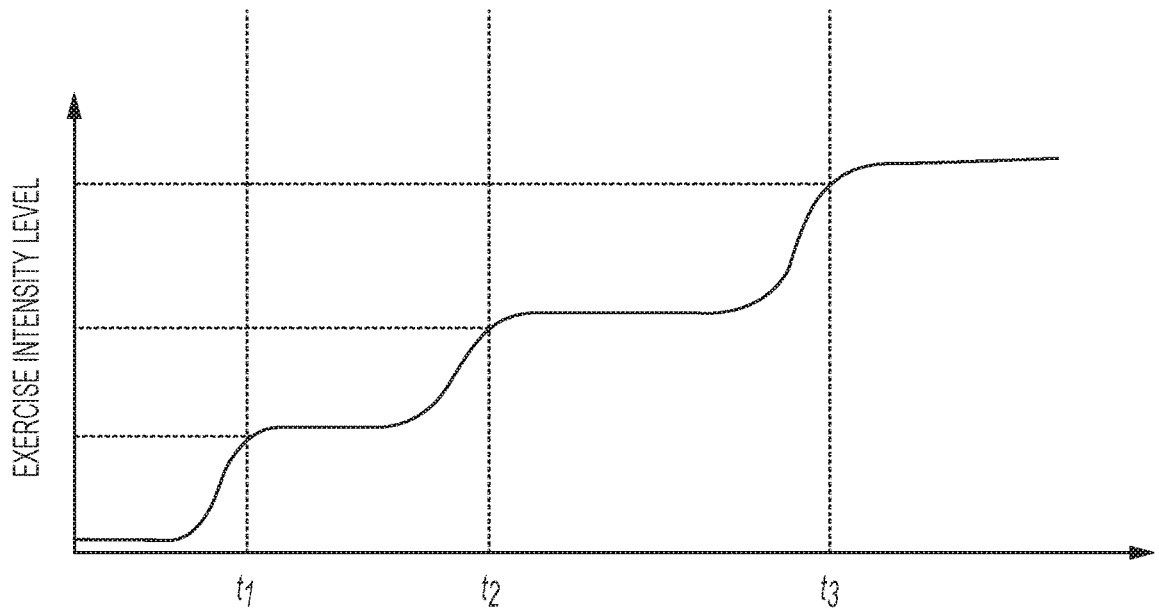
FIG. 9 is a graph of an exercise intensity metric with respect to time in accordance one exemplary embodiment.
Figure 10:
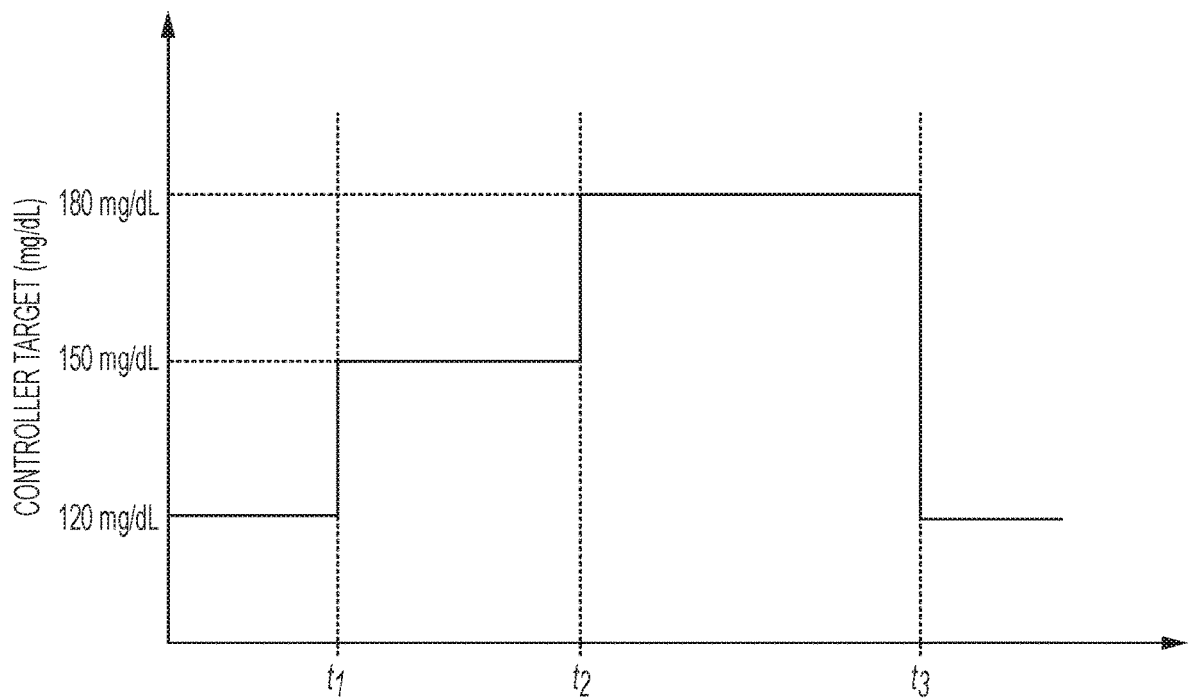
FIG. 10 is a graph of a target glucose value for a closed-loop control system with respect to time in accordance with one exemplary embodiment of the control process of FIG. 8 corresponding to the exercise intensity metric of FIG. 9.

FIG. 9 depicts an exemplary graph of an exercise intensity metric that may be calculated or otherwise determined based on measurement data from auxiliary sensing arrangements 506, 508, and FIG. 10 depicts an exemplary graph of a target glucose value for a closed-loop control system (e.g., target glucose value 702 of closed-loop control system 700) that may be dynamically adjusted in accordance with the control process 800 based on the value of the exercise intensity metric depicted in FIG. 9. Referring to FIGS. 9-10 with reference to FIGS. 5-7, prior to time $t_1$, the exercise intensity metric calculated by the exercise classification application 608 based on the current measurement values from the auxiliary sensing arrangements 506, 508 is less than a first threshold value indicative of the user being sedentary. At time $t_1$, the value for the exercise intensity metric increases above the first threshold value (e.g., due to changes to acceleration measurement values, heart rate measurement values, lactate measurement values, ketone measurement values, or the like), thereby causing the exercise classification application 608 to detect a change in the user's activity level and classify the user's current activity level as mild intensity exercise due to the exercise intensity metric value being greater than the first threshold value but less than a second threshold value indicative of moderate intensity exercise.

As illustrated in FIG. 10, at time $t_1$, in response to detecting and classifying the user's current activity level as mild exercise, the pump control system 520, 600 automatically adjusts the target glucose value 702 used by the closed-loop control system 700 by increasing the target glucose value 702 from 120 milligrams per deciliter (mg/dL) to 150 mg/dL to account for the user engaging in exercise. In this regard, increasing the target glucose value 702 influences the result output by the summation block 706 in a manner that decreases the commanded dosage output 730 by the closed-loop control system 700. Thereafter, the pump control system 520, 600 maintains closed-loop operation of the infusion device 502 using the adjusted controller target value of 150 mg/dL until detecting a subsequent change in the user's activity level.

At time $t_2$, the value for the exercise intensity metric increases above a second threshold value, thereby causing the exercise classification application 608 to detect a change in the user's activity level and classify the user's current activity level as moderate intensity exercise. As a result, at time $t_2$, the pump control system 520, 600 further increases the target glucose value 702 used by the closed-loop control system 700 from 150 mg/dL to 180 mg/dL account for the increased exercise intensity and the corresponding likelihood of the user's glucose level falling due to exercise without additional insulin infusion. In other words, the increased target glucose may effectively suspend insulin delivery during continued exercise absent indication of a potential hyperglycemic event (e.g., a measured glucose value 704 greater than 180 mg/dL) to avoid potential exercise-induced hypoglycemia.

Additionally or alternatively, at time $t_2$, the pump control system 520, 600 may automatically adjust one or more other control parameters utilized by the command generation application 610 to account for the increased exercise intensity. For example, the pump control system 520, 600 may decrease the time constant associated with the derivative path (e.g., by multiplying the time constant by a fractional scaling factor) to reduce the responsiveness of the closed-loop control system 700 increases in the measured glucose value 704. As described above, in some embodiments, the time constant is adjusted asymmetrically and dependent on the trend in the measured glucose values 704. For example, when the trend in the measured glucose values 704 is positive, the time constant associated with the derivative term may be reduced or scaled downward to make the derivative path component less aggressive or less responsive during moderate or aerobic exercise to avoid excess infusion of insulin, while maintaining the same time constant when the trend in the measured glucose values 704 is less than or equal to zero to maintain the same level of responsiveness for downward trends and further protect against exercise-induced hypoglycemia.

As another example, the pump control system 520, 600 may additionally or alternatively reduce one or more insulin delivery limits applied to the output 730 of the closed-loop control system 700 to further reduce the amount or rate of insulin infusion. For example, in some embodiments, the command generation application 610 may support a maximum dosage limit value for the output 730 that caps, restricts or otherwise limits the dosage command used for determining corresponding motor commands, and thus, lowering the maximum dosage limit value may operate to further reduce the insulin infusion rate or amount in concert with the adjustments to the target glucose value 702 and/or the derivative path time constant. As another example, the command generation application 610 may support a maximum amount of insulin delivered over a preceding time interval, which may be similarly lowered to effectively suspend or otherwise reduce the insulin infusion rate while the user is engaged in moderate exercise.

At time $t_3$, when the value for the exercise intensity metric increases above a third threshold value indicative of anaerobic or high intensity exercise, the exercise classification application 608 detects the change in the user's activity level and classify the user's current activity level as anaerobic or high intensity exercise. As a result, at time $t_3$, the pump control system 520, 600 adjusts one or more control parameters of used by the closed-loop control system 700 to mitigate or otherwise avoid exercise-induced hyperglycemia due to a decreased insulin response. For example, in the illustrated embodiment of FIG. 10, the pump control system 520, 600 automatically adjusts the target glucose value 702 by reverting the target glucose value 702 back to the original target glucose value 702 of 120 mg/dL that was previously programmed or determined for the user. Additionally, the pump control system 520, 600 may automatically restore time constants, maximum insulin delivery limits, and other control parameters to their original values further reduce the likelihood of exercise-induced hyperglycemia. Moreover, in various embodiments, the pump control system 520, 600 may adjust control parameters of the closed-loop control system 700 to increase responsiveness to increases in the measured glucose value 704. For example, the pump control system 520, 600 may multiply the time constant associated with the derivative path by a scaling factor greater than one to increase the responsiveness of the closed-loop control system 700 to mitigate increases in the measured glucose value 704. Maximum insulin delivery limits may also be relaxed or further increased to allow for a greater rate or amount of insulin infusion.

Thereafter, when the pump control system 520, 600 and/or the exercise classification application 608 detects a change in exercise level from an anaerobic or high intensity back to a lower intensity or sedentary level, the pump control system 520, 600 may automatically adjust the control parameters accordingly. In this regard, when the exercise intensity metric falls below the first threshold value, the exercise classification application 608 detects a sedentary state and automatically restores any of the control parameters that were adjusted during exercise back to their original or default values for the sedentary state, thereby restoring the closed-loop regulation of the user's glucose level to the normal state.

Again, it should be appreciated that there are numerous different control parameters or combinations thereof that may be adjusted to tune the responsiveness of a closed-loop control scheme to different exercise intensity levels, and moreover, numerous different manners in which such control parameters could be adjusted, scaled, or otherwise modified to achieve a desired controller behavior. Furthermore, there are numerous different manners in which exercise intensity could be determined and classified, and numerous different types or combinations of auxiliary sensing arrangements that may be utilized to detect and classify exercise intensity. Accordingly, the examples described herein are not intended to be exhaustive or limiting, and the subject matter described herein is not limited to any particular manner or type of exercise intensity classes or categories, any particular type or combination of sensing arrangements used to detect and classify exercise intensity or other activity levels, or any particular manner or type of control parameter adjustment.

It will be appreciated that the subject matter described herein allows for exercise or other activity potentially affecting glucose levels or insulin sensitivity to be automatically detected and classified according to their different impacts on insulin response or glucose levels using auxiliary sensing arrangements, with control information for providing closed-loop control of the user's blood glucose level being automatically adjusted based on the classification or categorization of the exercise intensity to account for the anticipated changes in the user's glucose levels or insulin response. Thus, potential hypoglycemic events due to mild-to-moderate aerobic exercise may be mitigated or avoided, while also allowing for potential exercise-induced hyperglycemic events resulting from anaerobic or higher intensity exercise to be mitigated or avoided by detecting and classifying changes in exercise intensity and dynamically adjusting closed-loop control information in real-time to account for the dynamic and variable nature of the body's response to exercise intensity.

For the sake of brevity, conventional techniques related to glucose sensing and/or monitoring, sensor calibration and/or compensation, and other functional aspects of the subject matter may not be described in detail herein. In addition, certain terminology may also be used in the herein for the purpose of reference only, and thus is not intended to be limiting. For example, terms such as "first," "second," and other such numerical terms referring to structures do not imply a sequence or order unless clearly indicated by the context. The foregoing description may also refer to elements or nodes or features being "connected" or "coupled" together. As used herein, unless expressly stated otherwise, "coupled" means that one element/node/feature is directly or indirectly joined to (or directly or indirectly communicates with) another element/node/feature, and not necessarily mechanically.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. For example, the subject matter described herein is not limited to the infusion devices and related systems described herein. Moreover, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application. Accordingly, details of the exemplary embodiments or other limitations described above should not be read into the claims absent a clear intention to the contrary.

What is claimed is:

1. A method of operating an infusion device capable of delivering fluid to a user, the fluid influencing a physiological condition of the user, the method comprising:
   obtaining, by a control system associated with the infusion device, one or more measurements indicative of a second condition of the user different from the physiological condition;
   classifying, by the control system, the second condition as one of a plurality of intensity levels based at least in part on the one or more measurements;
   obtaining, by the control system, a first measurement indicative of the physiological condition of the user from a first sensing arrangement;
   determining a trend associated with the physiological condition of the user based on the first measurement and one or more preceding measurements indicative of the physiological condition from the first sensing arrangement;
   adjusting a time constant associated with closed-loop control of the physiological condition, resulting in an adjusted time constant, wherein adjusting the time constant comprises:
      adjusting the time constant to decrease responsiveness of the closed-loop control when the trend is positive; and
      maintaining the time constant when the trend is negative; and
   determining a command for operating a motor of the infusion device based on a difference between the first measurement and a target value using the closed-loop control with the adjusted time constant.

2. The method of claim 1, further comprising adjusting the target value based on the one of the plurality of intensity levels, resulting in an adjusted target value, wherein determining the command comprises determining the command for operating the motor of the infusion device based on a difference between the first measurement and the adjusted target value using the closed-loop control with the adjusted time constant.

3. The method of claim 2, wherein adjusting the target value comprises increasing the target value in response to classifying the second condition as aerobic exercise.

4. The method of claim 2, wherein adjusting the target value comprises decreasing the target value in response to classifying the second condition as anaerobic exercise.

5. The method of claim 1, wherein adjusting the time constant comprises decreasing the time constant in response to classifying the second condition as aerobic exercise.

6. The method of claim 1, wherein adjusting the time constant comprises increasing the time constant in response to classifying the second condition as anaerobic exercise.

7. The method of claim 1, further comprising:
   decreasing a delivery limit in response to classifying the second condition as aerobic exercise; and
   limiting the command in accordance with the decreased delivery limit.

8. The method of claim 1, further comprising increasing a delivery limit in response to classifying the second condition as anaerobic exercise, wherein determining the command comprises determining the command for operating a motor of the infusion device based on the difference between the first measurement and the target value for the physiological condition in accordance with the increased delivery limit.

9. A method of operating an infusion device, the method comprising:
   obtaining, by a control system associated with the infusion device, a current glucose measurement from a glucose sensing arrangement;
   obtaining, by the control system, one or more measurements from an auxiliary sensing arrangement different from the glucose sensing arrangement;
   detecting, by the control system, aerobic exercise based at least in part on the one or more measurements; and
   operating, by the control system, an actuation arrangement of the infusion device to deliver insulin to regulate a glucose level based on the current glucose measurement by decreasing a rate or amount of insulin delivery in response to detecting aerobic exercise, wherein decreasing the rate or amount of insulin delivery comprises decreasing a derivative time constant associated with proportional-integral-derivative (PID) control of the actuation arrangement of the infusion device to regulate the current glucose measurement to a target glucose value.

10. The method of claim 9, wherein decreasing the rate or amount of insulin delivery comprises increasing the target glucose value associated with closed-loop control of the actuation arrangement of the infusion device to regulate the current glucose measurement to the increased target glucose value.

11. The method of claim 9, further comprising:
   detecting anaerobic exercise based at least in part on the one or more measurements; and
   increasing a rate or amount of insulin delivery in response to detecting anaerobic exercise.

12. The method of claim 11, wherein increasing the rate or amount of insulin delivery comprises decreasing the target glucose value associated with closed-loop control of the actuation arrangement of the infusion device to regulate the current glucose measurement to the decreased target glucose value.

13. The method of claim 11, wherein increasing the rate or amount of insulin delivery comprises increasing a delivery limit associated with closed-loop control of the actuation arrangement of the infusion device to regulate the current glucose measurement to the target glucose value.

14. An infusion system comprising:
   an actuation arrangement operable to deliver insulin to a user;
   a glucose sensing arrangement to obtain a measured glucose value for the user;
   a second sensing arrangement to obtain measurement data indicative of exercise by the user; and
   a control system coupled to the actuation arrangement, the glucose sensing arrangement, and the second sensing arrangement to:

classify the exercise by the user as a first level of a plurality of levels of exercise intensity based on the measurement data;

determining a trend associated with a glucose level of the user based on the measured glucose value and one or more preceding measured glucose values indicative of the glucose level from the glucose sensing arrangement;

adjust a time constant associated with closed-loop control of the glucose level of the user to decrease responsiveness of the closed-loop control when the trend is positive, resulting in an adjusted time constant; and determine a command for operating the actuation arrangement to deliver the insulin to the user based at least in part on a difference between the measured glucose value and a target glucose value using the closed-loop control with the adjusted time constant.

15. The infusion system of claim 14, wherein the second sensing arrangement comprises a lactate sensing arrangement or a ketone sensing arrangement.

* * * * *